United States Patent [19]
Crea

[11] Patent Number: 5,798,208
[45] Date of Patent: Aug. 25, 1998

[54] WALK-THROUGH MUTAGENESIS

[75] Inventor: Roberto Crea, 45 Amherst Rd., Belmont, Mass. 02178-2102

[73] Assignee: Roberto Crea, San Mateo, Calif.

[21] Appl. No.: 930,600

[22] Filed: Nov. 2, 1992

Related U.S. Application Data

[63] Continuation-in-part of Ser. No. 505,314, Apr. 5, 1990, abandoned.

[51] Int. Cl.$^6$ .............................. C12Q 1/68; C12P 19/34; C12P 21/00
[52] U.S. Cl. .................. 435/6; 435/91.2; 435/69.1
[58] Field of Search .................. 435/6, 69.1, 172.3, 435/252.3, 287, 91.1, 91.2; 536/23.2, 25.3

[56] References Cited

U.S. PATENT DOCUMENTS

| | | | |
|---|---|---|---|
| 4,744,037 | 5/1988 | Niina et al. | 364/497 |
| 5,096,815 | 3/1992 | Ladner et al. | 435/69.1 |
| 5,264,563 | 11/1993 | Huse | 536/25.3 |

FOREIGN PATENT DOCUMENTS

| | | |
|---|---|---|
| WO 89/10754 | 11/1989 | WIPO. |
| WO 90/02809 | 3/1990 | WIPO. |
| 90/07862 | 7/1990 | WIPO. |

OTHER PUBLICATIONS

Harris, T.J.R. "Catalytic Antibodies—Something for Everyone", *Trends in Biotechnology*, 9: 39–41 (Feb. 1991).
Knowles, J.R. "Tinkering with Enzymes: What Are We Learning", *Science* 236: 1253–1258 (Jun. 5, 1987).
Blacklow et al., (1990), "Manipulative Mutagenesis of Enzymes". In: *Protein & Pharmaceutical Engineering*, Craik et al., Eds. (Wiley-Liss: New York) pp. 159–166.
Cunningham, B.C. et al., "Receptor and Antibody Epitopes in Human Growth Hormone Identified by Homolog-Scanning Mutagenesis", *Science* 243: 1330–1336 (Mar. 10, 1989).
Cunnigham, B.C. et al. "High-Resolution Epitope Mapping of hGH-Receptor Interactions by Alanine-Scanning Mutagenesis", *Science* 244: 1081–1085 (Jun. 2, 1989).
I.S. Dunn et al., "Imroved Peptide Function from Random Mutagenesis Over Short 'Windows', " *Protein Engineering* 2(4): 283–291 (1988).
A.R. Oliphant et al., "An Efficient Method for Generating Proteins with Altered Enezymatic Properties: Application to β-Lactamase." *Proc. Nat'l Acad. Sci. USA*, 86: 9044–9098 (Dec. 1989).
P.M. Lehtovaara et al., "A New Method for Random Mutagenesis of Complete Genes: Enzymatic Generation of Mutant Libraries in Vitro", *Protein Engineering*, 2: 63–68 (1988).

T.A. Craig et al., "Site-Specific Mutagenesis of the α-Helices of Calmodulin," *J. of Biol. Chem.*, 262(7): 3278–3284 (Mar. 5, 1987).
R.J. Kuhn et al., "Construction of a 'mutagenesis cartridge' 'for Poliovirus Genome–linked Viral Protein: Isolation and Characterization . . . " *Proc. Natl. Acad. Sci. USA* 85: 519–523 (Jan. 1988).
R. Murray et al., "Random Oligonucleotide Mutagenesis: Application to a Large Protein Coding Sequence of a Major Histocompatibility Complex Class I Gene, H–2DP," *Nucleic Acids Research*, 16(20): 9761–9773 (1988).
J.F. Reidhaar–Olson et al., "Conbinatorial Cassette Mutagenesis as a Probe of the Informational Content of Protein Sequences" *Science*, 241: 53–57 (Jul. 1, 1988).
A.R. Oliphant et al., "The Use of Random-Sequence Oligonucleotides for Determining Consensus Sequences," *Methods in Enzymology* 155: 568–583 (1987).
D.E. Hill et al., "Mutagenesis with Degenerate Oligonucleotides: An Efficient Method for Saturating a Defined DNA Region with Base Pair Substitutions" *Methods in Enzymology* 155: 558–569 (1987).
Wm.D. Huse et al., "Generation of a Large Combinatorial Library of the Immunoglobulin Repertoire in Phage Lambda" *Science* 246: 1275–1281 (Dec. 8, 1989).
J.M. Jacobs, "New Perspectives on Catalytic Antibodies" *Bio/Technology* 9: 258–262 (Mar. 1991).
E. Baldwin et al., "Generation of a Catalytic Antibody by Site-Directed Mutagenesis" *Science* 245: 1104–1107 (Sep. 8, 1989).
B.L. Iverson et al., "Metalloantibodies" *Science* 249: 659–662 (Aug. 10, 1990).
Heemes et al., Gene 84: 143–151 (1989) "A reliable method for random Mutagenesis . . . ".

*Primary Examiner*—Eggerton A. Campbell
*Attorney, Agent, or Firm*—Hamilton, Brook, Smith & Reynolds, P.C.

[57] ABSTRACT

A method of mutagenesis by which a predetermined amino acid is introduced into each and every position of a selected set of positions in a preselected region (or several different regions) of a protein to produce library of mutants. The method is based on the premise that certain amino acids play crucial role in the structure and fuction of proteins. Libraries can be generated which contain a high proportion of the desired mutants and are of reasonable size for screening. This libraries can be used to study the role of specific amino acids in protein structure and function and to develop new or improved proteins and polypeptides such as enzymes, antibodies, single chain antibodies and catalytic antibodies.

33 Claims, 16 Drawing Sheets

FIG. 3A

| VH CDR1 | 31 | 32 | 33 | 34 | 35 | |
|---|---|---|---|---|---|---|
| | ASP | PHE | TYR | MET | GLU | (AMINO ACID SEQUENCE) |
| | GAC | TTC | TAC | ATG | GAG | (DNA SEQUENCE) |
| ASP WALK-THROUGH (GAC, GAT) | --- | GA- | G-- | GAT | --T | |
| MIXED PROBE | GAC | TT C GA | T AC G | ATG GA GAT | G T | 128 OLIGONUCLEOTIDE SEQUENCES |
| AMINO ACIDS | 1 | 4 | 2 | 7 | 2 | 112 DIFFERENT PEPTIDE SEQUENCES |
| | ASP | PHE ASP TYR VAL | TYR ASP | MET ASP VAL GLU ASN ILE LYS | GLU ASP | |
| % ASP OCCURRENCE | 100 | 25 | 50 | 12.5 | 50 | |

FIG. 3B

| VH CDR3 | 101 | 102 | 103 | 104 | 105 | 106 | 107 | 108 | 109 | 110 | 111 | |
|---|---|---|---|---|---|---|---|---|---|---|---|---|
| | ASN | TYR | TYR | GLY | SER | THR | TRP | TYR | PHE | ASP | VAL | (AMINO ACID SEQUENCE) |
| | AAC | TAC | TAT | GGC | AGC | ACT | TGG | TAC | TTC | GAC | GTT | (DNA SEQUENCE) |
| SER WALK-THROUGH (TCX and AG$^T_C$) | -G- | -C- | -C- | A-- | --- | -G- | -C- | -C- | -C- | TC- | TC- | |
| MIXED PROBE | A<br>A<br>C<br>G | A<br>T<br>C | A<br>T<br>C<br>C | GC<br>A | G | C<br>G | A<br>T T G<br>G | T<br>A<br>T C<br>C | G A<br>T C T C<br>C C | GA<br>TC<br>TC | GT<br>T<br>TC | $2^{12} = 4{,}096$ OLIGONUCLEOTIDES |
| AMINO ACIDS | 2 | 2 | 2 | 2 | 1 | 2 | 2 | 2 | 2 | 4 | 4 | 4,096 PEPTIDE SEQUENCES |
| | ASN<br>SER | TYR<br>SER | TYR<br>SER | GLY<br>SER | SER | THR<br>SER | TRP<br>SER | TYR<br>SER | PHE<br>SER | ASP<br>SER<br>ALA<br>TYR | VAL<br>SER<br>ALA<br>PHE | |
| % SER | 50 | 50 | 50 | 50 | 100 | 50 | 50 | 50 | 50 | 25 | 25 | |

FIG. 3C

| VL CDR2 | 56 | 57 | 58 | 59 | 60 | 61 | 62 | |
|---|---|---|---|---|---|---|---|---|
| | GLY | ALA | SER | THR | ARG | GLU | SER | (AMINO ACID SEQUENCE) |
| HIS WALK-THROUGH (CAC, CAT) | GGT | GCT | AGC | ACC | CGT | GAA | TCT | (DNA SEQUENCE) |
| | CA- | CA- | CA- | CA- | -A- | C-T | CA- | |
| MIXED PROBE | GG<br>T | GC<br>CA | AG<br>C<br>CA | AC<br>C<br>CA | G<br>C<br>A | G A TC<br>C C T A T<br>A C T CA | T<br>CA | 8,192 OLIGONUCLEOTIDES |
| AMINO ACIDS | 4 | 4 | 4 | 4 | 2 | 4 | 4 | |
| | GLY | ALA | SER | THR | ARG | GLU | SER | 8,192 PEPTIDE SEQUENCES |
| | HIS | HIS | HIS | HIS | HIS | HIS | HIS | |
| | ARG | ASP | ARG | PRO | | ASP | PRO | |
| | ASP | ALA | ASN | ASN | | HIS | TYR | |
| % HIS | 25 | 25 | 25 | 25 | 50 | 25 | 25 | |

FIG. 4A

| VH CDR3 | 101 | 102 | 103 | 104 | 105 | 106 | 107 | 108 | 109 | 110 | 111 | |
|---|---|---|---|---|---|---|---|---|---|---|---|---|
| | ASN | TYR | TYR | GLY | SER | THR | TRP | TYR | PHE | ASP | VAL | (AMINO ACID SEQUENCE) |
| | AAC | TAC | TAT | GGC | AGC | ACT | TGG | TAC | TTC | GAC | GTT | (DNA SEQUENCE) |
| HIS WALK-THROUGH (CAT, CAC) | C-- | C-- | C-- | CA- | CA- | CA- | CAT | C-- | CA- | C-- | CA- | |
| MIXED OLIGO | A<br>AC<br>C | T<br>AC<br>C | T<br>AT<br>C | GG<br>C<br>CA | AG<br>C<br>CA | AC<br>T<br>CA | TGG<br>CAT | T<br>AC<br>C | TT<br>C<br>CA | G<br>AC<br>C | GT<br>CA | T = 2^18 OR 262,144 OLIGONUCLEOTIDES |
| AMINO ACIDS | 2 | 2 | 2 | 4 | 4 | 4 | 6 | 2 | 4 | 2 | 4 | VAL = 196,608 DIFFERENT PEPTIDE SEQUENCES |
| | ASN<br>HIS | TYR<br>HIS | TYR<br>HIS | GLY<br>HIS<br>ARG<br>ASP | SER<br>HIS<br>ARG<br>ASN | THR<br>HIS<br>ASN<br>PRO | TRP<br>HIS<br>ARG<br>CYS<br>GLN<br>TYR | TYR<br>HIS | PHE<br>HIS<br>LEU<br>TYR | ASP<br>HIS | VAL<br>HIS<br>ASP<br>LEU | |
| % HIS | 50 | 50 | 50 | 25 | 25 | 25 | 14.2 | 50 | 25 | 50 | 25 | |

FIG. 4B

| VL CDR2 | 55 | 56 | 57 | 58 | 59 | 60 | 61 | 62 | |
|---|---|---|---|---|---|---|---|---|---|
| | TYR | GLY | ALA | SER | THR | ARG | GLU | SER | (AMINO ACID SEQUENCE) |
| | TAC | GGT | GCT | AGC | ACC | CGT | GAA | TCT | (DNA SEQUENCE) |
| SER WALK-THROUGH (AGT, AGC, TCX) | -C- | A-- | T-- | --- | -G- | A-- | TC- | --- | |
| MIXED OLIGO | T$^A_C$C | $^G_A$GT | $^G_T$CT | AGC | A$^C_G$C | $^C_A$GT | $^{GA}_{TC}$A | TCT | = $2^7$ or 128 OLIGONUCLEOTIDES |
| AMINO ACIDS | 2 | 2 | 2 | 1 | 2 | 2 | 3 | 1 | = 96 DIFFERENT PEPTIDE SEQUENCES |
| | TYR | GLY | ALA | SER | THR | ARG | GLU | SER | |
| | SER | SER | SER | | SER | SER | SER | | |
| | | | | | | | ALA | | |
| % SER | 50 | 50 | 50 | 100 | 50 | 50 | 33.3 | 100 | |

FIG. 5A

| VH CDR2 | 55 | 56 | 57 | 58 | 59 | 60 | 61 | 62 | 63 | 64 | 65 | 66 | 67 | 68 | |
|---|---|---|---|---|---|---|---|---|---|---|---|---|---|---|---|
| | GLY | ASN | LYS | TYR | THR | THR | GLU | TYR | SER | ALA | SER | VAL | LYS | GLY | (AMINO ACID SEQUENCE) |
| | GGT | AAC | AAG | TAT | ACT | ACT | GAA | TAC | AGC | GCT | TCT | GTT | AAA | GGT | (DNA SEQUENCE) |
| HIS WALK-THROUGH (CAC, CAT) | CA- | C-- | C-T | C-- | CA- | CA- | C-T | C-- | CA- | CA- | CA- | CA- | C-C | CA- | |
| MIXED OLIGO | GG A<br>T AC<br>CA C | A<br>AC<br>C | A G<br>A<br>C T<br>C | T<br>AT<br>C | AC<br>T<br>CA | AC<br>T<br>CA | A G A<br>T A<br>C T C | T<br>AC<br>C | AG<br>CA | GC<br>C<br>CA | TC<br>T<br>CA | GT<br>T<br>CA | A A<br>A<br>C C | GG<br>T = 2²⁵ OLIGONUCLEOTIDES<br>CA | |
| AMINO ACIDS | 4 | 2 | 4 | 2 | 4 | 4 | 4 | 4 | 2 | 4 | 4 | 4 | 4 | 4 = 2²⁵ DIFFERENT PEPTIDE SEQUENCES | |
| | GLY<br>HIS<br>ARG<br>ASP | ASN<br>HIS<br>ASN<br>GLY | LYS<br>HIS<br>ASN | TYR<br>HIS | THR<br>HIS<br>ASN<br>PRO | THR<br>HIS<br>ASN<br>PRO | GLU<br>HIS<br>ASP<br>GLN | TYR<br>HIS | SER<br>HIS<br>ARG | ALA<br>HIS<br>ASP<br>TYR | SER<br>HIS<br>PRO<br>LEU | VAL<br>HIS<br>TYR<br>GLN | LYS<br>HIS<br>ASN<br>ASP | GLY<br>HIS<br>ARG<br>ASP | |
| % HIS | 25 | 50 | 25 | 50 | 25 | 25 | 25 | 50 | 25 | 25 | 25 | 25 | 25 | 25 | |

FIG. 5B

| VH CDR 2 | 50 | 51 | 52 | 53 | 54 | 55 | 56 | 57 | 58 | 59 | 60 | |
|---|---|---|---|---|---|---|---|---|---|---|---|---|
| | ALA | SER | ARG | ASN | LYS | GLY | ASN | LYS | TYR | THR | THR | (AMINO ACID SEQUENCE) |
| | GCT | TCT | CGT | AAC | AAA | GGT | AAC | AAG | TAT | ACC | ACT | (DNA SEQUENCE) |
| HIS WALK-THROUGH (CAT, CAC) | CA— | — — — | —A— | — — — | — — — | — — — | C— — | — — — | C— — | — — — | CA— | |
| MIXED OLIGO | GC$^T_A$ CA | TCT | $^G_A$C$^T_A$ | AAC | AAA | GGT | A$^{AC}_C$ | AAG | $^T_C$AT | ACC | AC$^T_A$ CA | T = $2^7$ OR 128 OLIGONUCLEOTIDES |
| AMINO ACIDS | 4 | 1 | 2 | 1 | 1 | 1 | 2 | 1 | 2 | 1 | 4 | = 128 DIFFERENT PEPTIDE SEQUENCES |
| | ALA HIS ASP PRO | SER | ARG HIS | ASN | LYS | GLY | ASN HIS | LYS | TYR HIS | THR | THR HIS ASN PRO | |
| % HIS | 25 | | 50 | | | | 50 | | 50 | | 25 | |

FIG. 6

| VH CDR2 | 50 | 51 | 52 | 53 | 54 | 55 | 56 | 57 | 58 | 59 | 60 | (AMINO ACID SEQUENCE) |
|---|---|---|---|---|---|---|---|---|---|---|---|---|
| | ALA | SER | ARG | ASN | LYS | GLY | ASN | LYS | TYR | THR | THR | |
| | GCT | TCT | CGT | AAC | AAA | GGT | AAC | AAG | TAT | ACC | ACT | (DNA SEQUENCE) |
| SER WALK-THROUGH (AGC, AGT, TCX) | T-- | --- | A-- | -G- | -GC | A-- | -G- | -GC | -C- | -G- | -G- | |
| MIXED OLIGO | G CT T | TCT | C GT A | A C A G | AA A GC | G GT A | A C A G | AG A GC | A T T C | C A C G | C A T G | |
| AMINO ACIDS | 2 | 1 | 2 | 2 | 4 | 2 | 2 | 4 | 2 | 2 | 2 | = 4096 OLIGONUCLEOTIDES |
| | ALA SER | SER | ARG SER | ASN SER | LYS SER ARG ASN | GLY SER | ASN SER | LYS SER ARG ASN | TYR SER | THR SER | THR SER | = 4096 DIFFERENT PEPTIDE SEQUENCE |
| % SER | 50 | 100 | 50 | 50 | 25 | 50 | 50 | 25 | 50 | 50 | 50 | |

FIG. 7
ACTIVE SITE

| | | | | |
|---|---|---|---|---|
| HIV PROTEASE | ASP | THR | GLY | (AMINO ACID SEQUENCE) |
| | GAC | ACT | GGT | (DNA SEQUENCE) |
| ASP WALK-THROUGH (GAC, GAT) | --- | GA- | -A- | |
| HIS WALK-THROUGH (CAC, CAT) | C-- | CA- | CA- | |
| SER WALK-THROUGH (AGT, AGC, TCX) | TC- | -G- | A-- | |
| MIXED OLIGO | C<br>TC<br>GAC | GA<br>CG<br>ACT | C<br>AA<br>GGT | |
| | 6 | 9 | 6 | = 324 OLIGONUCLEOTIDES |
| AMINO ACIDS | ASP<br>HIS<br>SER<br>ALA<br>PRO<br>TYR | THR<br>ASP<br>HIS<br>SER<br>ALA<br>ARG<br>ASN<br>GLY<br>PRO | GLY<br>ASP<br>HIS<br>SER<br>ARG<br>ASN | = 324 DIFFERENT PEPTIDE SEQUENCES |
| % ASP<br>% HIS<br>% SER | 16.6<br>16.6<br>16.6 | 11.1<br>11.1<br>11.1 | 16.6<br>16.6<br>16.6 | |

FIG. 8A

| VL CDR1 | 34 | 35 | 36 | 37 | 38 | 39 | 40 | |
|---|---|---|---|---|---|---|---|---|
| | ASN | GLN | LYS | ASN | PHE | LEU | ALA | (AMINO ACID SEQUENCE) |
| | AAC | CAG | AAG | AAC | TTC | CTG | GCT | (DNA SEQUENCE) |
| SER WALK-THROUGH (AGC, AGT, TCX) | -G- | TC- | -GT | -G- | -C- | --- | T-- | |
| HIS WALK-THROUGH (CAC, CAT) | C-- | --T | C-T | C-- | CA- | --- | CA- | |
| MIXED OLIGO | G<br>AAC<br>C | TC<br>CAG<br>T | GT<br>AAG<br>C | G<br>AAC<br>C | C<br>TTC<br>CA | CTG | T<br>GCT<br>CA | = 36,864 OLIGONUCLEOTIDES |
| | 4 | 5 | 6 | 4 | 6 | 1 | 6 | |
| AMINO ACIDS | ASN<br>SER<br>HIS<br>ARG | GLN<br>SER<br>HIS<br>PRO<br>TYR | LYS<br>SER<br>HIS<br>ARG<br>ASN<br>GLN | ASN<br>SER<br>HIS<br>ARG | PHE<br>SER<br>HIS<br>LEU<br>PRO<br>TYR | LEU | ALA<br>SER<br>HIS<br>ASP<br>PRO<br>TYR | = 17,280 DIFFERENT PEPTIDE SEQUENCES |
| % SER | 25 | 28.5 | 12.5 | 25 | 16.6 | | 16.6 | |
| % HIS | 25 | 14.2 | 12.5 | 25 | 16.6 | | 16.6 | |

FIG. 8B

| VL CDR3 | 95 | 96 | 97 | 98 | 99 | 100 | 101 | 102 | |
|---|---|---|---|---|---|---|---|---|---|
| | GLN | ASN | ASP | HIS | SER | TYR | PRO | LEU | (AMINO ACID SEQUENCE) |
| | CAA | AAC | GAC | CAC | TCT | TAC | CCG | CTT | (DNA SEQUENCE) |
| ASP WALK-THROUGH (GAT, GAC) | G--C | --- | --- | G-- | GA- | G-- | --- | GA- | |
| SER WALK-THROUGH (AGT, AGC, TCX) | TC- | --- | TC- | AG- | --- | -C- | --- | AG- | |
| MIXED OLIGO | G<br>CAA<br>TC | C<br>AAC | G<br>GAC<br>TC | CAC<br>AG | GA<br>TCT<br>AG | G<br>TAC<br>C | TAC<br>C | GA<br>CTT<br>AG | |
| | 8 | 1 | 4 | 6 | 4 | 4 | 1 | 9 | = 41,472 OLIGONUCLEOTIDES |
| AMINO ACIDS | GLN<br>ASP<br>SER<br>HIS<br>GLU<br>ALA<br>PRO<br>TYR | ASN | ASP<br>SER<br>ALA<br>TYR<br>ASN<br>GLY | HIS<br>ASP<br>SER<br>ARG | SER<br>ASP<br>ALA<br>TYR | TYR<br>ASP<br>SER<br>ALA | PRO | LEU<br>ASP<br>SER<br>ARG<br>ASN<br>GLY<br>HIS<br>ILE<br>Val | = 27,648 DIFFERENT PEPTIDE SEQUENCES |
| % ASP | 9 | | 25 | 16.6 | 25 | 25 | | 11 | |
| % SER | 18 | | 25 | 16.6 | 25 | 25 | | 11 | |

FIG. 8C

| VH CDR1 | 31 | 32 | 33 | 34 | 35 | |
|---|---|---|---|---|---|---|
| | ASP | PHE | TYR | MET | GLU | |
| | GAC | TTC | TAC | ATG | GAG | (DNA SEQUENCE) |
| ASP WALK-THROUGH (GAT, GAC) | --- | GA- | G-- | --- | --T | |
| HIS WALK-THROUGH (CAC, CAT) | C-- | CA- | C-- | --- | C-T | |
| SER WALK-THROUGH (AGT, AGC, TCX) | --- | -C- | -C- | --- | --- | |
| MIXED OLIGO | C GAC | GA CC TTC | G CC TAC | ATG | C T GAG | |
| | 2 | 9 | 6 | 1 | 4 | = 432 OLIGONUCLEOTIDES |
| AMINO ACIDS | ASP HIS | PHE ASP HIS SER ALA LEU PRO TYR VAL | TYR ASP HIS SER ALA PRO | MET | GLU ASP HIS GLN | = 432 DIFFERENT PEPTIDE SEQUENCES |
| % ASP | 50 | 11.1 | 16.6 | | 25 | |
| % HIS | 50 | 11.1 | 16.6 | | 25 | |
| % SER | 0 | 11.1 | 16.6 | | 0 | |

FIG. 8D

| VH CDR2 | 50 | 51 | 52 | 53 | 54 | 55 | 56 | 57 | 58 | 59 | 60 | |
|---|---|---|---|---|---|---|---|---|---|---|---|---|
| | ALA | SER | ARG | ASN | LYS | GLY | ASN | LYS | TYR | THR | THR | (AMINO ACID SEQUENCE) |
| | GCX | TCT | CGX | AAC | AAA | GGT | AAC | AAG | TAT | ACC | ACX | (DNA SEQUENCE) |
| HIS WALK-THROUGH (CAT, CAC) | CA- | --- | -A- | --- | --- | --- | C-- | --- | C-- | --- | CA- | |
| SER WALK-THROUGH (AGT, AGC, TCX) | T-- | --- | A-- | --- | --- | --- | -G- | --- | -C- | --- | -G- | |
| MIXED OLIGO | CA GCT T | TCT | A CGT A | AAC | AAA | GGT | C AAC G | AAG | C TAT C | ACC | CA ACT G | |
| AMINO ACIDS | 6 | 1 | 4 | 1 | 1 | 1 | 4 | 1 | 4 | 1 | 6 | =2304 OLIGONUCLEOTIDES =2304 DIFFERENT PEPTIDE SEQUENCES |
| | ALA HIS SER ASP PRO TYR | SER | ARG HIS SER ASN | ASN | LYS | GLY | ASN HIS SER ARG | LYS | TYR HIS SER PRO | THR | THR HIS SER ARG ASN PRO | |
| % HIS | 16.6 | | 25 | | | | 25 | | 25 | | 16.6 | |
| % SER | 16.6 | | 25 | | | | 25 | | 25 | | 16.6 | |

FIG. 8E

| VH CDR3 | 101 | 102 | 103 | 104 | 105 | |
|---|---|---|---|---|---|---|
| | ASN | TYR | TYR | GLY | SER | (AMINO ACID SEQUENCE) |
| | AAC | TAC | TAT | GGX | TCX | (DNA SEQUENCE) |
| ASP WALK-THROUGH (GAT, GAC) | G-- | G-- | G-- | -A- | GA- | |
| HIS WALK-THROUGH (CAC, CAT) | C-- | C-- | C-- | CA- | CA- | |
| SER WALK-THROUGH (AGT, AGC, TCX) | -G- | -C- | -C- | A-- | --- | |
| MIXED OLIGO | G<br>CG<br>AAC | G<br>CC<br>TAC | G<br>CC<br>TAT | C<br>AA<br>GGT | G<br>CA<br>TCC | |
| | 6 | 6 | 6 | 6 | 6 | = 7776 OLIGONUCLEOTIDES |
| AMINO ACIDS | ASN<br>ASP<br>HIS<br>SER<br>ARG<br>GLY | TYR<br>ASP<br>HIS<br>SER<br>ALA<br>PRO | TYR<br>ASP<br>HIS<br>SER<br>ALA<br>PRO | GLY<br>ASP<br>HIS<br>SER<br>ARG<br>ASN | SER<br>ASP<br>HIS<br>ALA<br>PRO<br>TYR | = 7776 DIFFERENT PEPTIDE SEQUENCES |
| % ASP | 16.6 | 16.6 | 16.6 | 16.6 | 16.6 | |
| % HIS | 16.6 | 16.6 | 16.6 | 16.6 | 16.6 | |
| % SER | 16.6 | 16.6 | 16.6 | 16.6 | 16.6 | |

WALK-THROUGH MUTAGENESIS

RELATED APPLICATIONS

This application is a 371 of PCT/US91/02,362, which is a continuation-in-part of U.S. Ser. No. 07/505,314, filed Apr. 5, 1990, now abandoned.

BACKGROUND OF THE INVENTION

Mutagenesis is a powerful tool in the study of protein structure and function. Mutations can be made in the nucleotide sequence of a cloned gene encoding a protein of interest and the modified gene can be expressed to produce mutants of the protein. By comparing the properties of a wild-type protein and the mutants generated, it is often possible to identify individual amino acids or domains of amino acids that are essential for the structural integrity and/or biochemical function of the protein, such as its binding and/or catalytic activity.

Mutagenesis, however, is beset by several limitations. Among these are the large number of mutants that can be generated and the practical inability to select from these, the mutants that will be informative or have a desired property. For instance, there is no reliable way to predict whether the substitution, deletion or insertion of a particular amino acid in a protein will have a local or global effect on the protein, and therefore, whether it will be likely to yield useful information or function.

Because of these limitations, attempts to improve properties of a protein by mutagenesis have relied mostly on the generation and analysis of mutations that are restricted to specific, putatively important regions of the protein, such as regions at or around the active site of the protein. But, even though mutations are restricted to certain regions of a protein, the number of potential mutations can be extremely large, making it difficult or impossible to identify and evaluate those produced. For example, substitution of a single amino acid position with all the other naturally occurring amino acids yields 19 different variants of a protein. If several positions are substituted at once, the number of variants increases exponentially. For substitution with all amino acids at seven amino acid positions of a protein, $19 \times 19 \times 19 \times 19 \times 19 \times 19 \times 19$ or $8.9 \times 10^8$ variants of the protein are generated, from which useful mutants must be selected. It follows that, for an effective use of mutagenesis, the type and number of mutations must be subjected to some restrictive criteria which keep the number of mutant proteins generated to a number suitable for screening.

A method of mutagenesis that has been developed to produce very specific mutations in a protein is site-directed mutagenesis. The method is most useful for studying small sites known or suspected to be involved in a particular protein function. In this method, nucleotide substitutions (point mutations) are made at defined locations in a DNA sequence in order to bring about a desired substitution of one amino acid for another in the encoded amino acid sequence. The method is oligonucleotide-mediated. A synthetic oligonucleotide is constructed that is complementary to the DNA encoding the region of the protein where the mutation is to be made, but which bears an unmatched base(s) at the desired position(s) of the base substitution(s). The mutated oligonucleotide is used to prime the synthesis of a new DNA strand which incorporates the change(s) and, therefore, leads to the synthesis of the mutant gene. See Zoller, M. J. and Smith, M., *Meth. Enzymol.* 100, 468 (1983).

Variations of site-directed mutagenesis have been developed to optimize aspects of the procedure. For the most part, they are based on the original methods of Hutchinson, C. A. et al., *J. Biol. Chem.* 253: 6551 (1978) and Razin, A. et al., *Proc. Natl. Acad. Sci. USA* 75: 4268 (1978). For an extensive description of site-directed mutagensis, see *Molecular Cloning A Laboratory Manual*, 1989, Sambrook, Fritsch and Maniatis, Cold Spring Harbor, N.Y., chapter 15.

A method of mutagenesis designed to produce a larger number of mutations is the "saturation" mutagenesis. This process is oligonucleotide-mediated also. In this method, all possible point mutations (nucleotide substitutions) are made at one or more positions within DNA encoding a given region of a protein. These mutations are made by synthesizing a single mixture of oligonucleotides which is inserted into the gene in place of the natural segment of DNA encoding the region. At each step in the synthesis, the three non-wild type nucleotides are incorporated into the oligonucleotides along with the wild type nucleotide. The non-wild type nucleotides are incorporated at a predetermined percentage, so that all possible variations of the sequence are produced with anticipated frequency. In this way, all possible nucleotide substitutions are made within a defined region of a gene, resulting in the production of many mutant proteins in which the amino acids of a defined region vary randomly (Oliphant, A. R. et al., *Meth. Enzymol.* 155: 568 (1987)).

Methods of random mutagenesis, such as saturation mutagenesis, are designed to compensate for the inability to predict where mutations should be made to yield useful information or functional mutants. The methods are based on the principle that, by generating all or a large number of the possible variants of relevant protein domains, the proper arrangement of amino acids is likely to be produced as one of the randomly generated mutants. However, for completely random combinations of mutations, the numbers of mutants generated can overwhelm the capacity to select meaningfully. In practice, the number of random mutations generated must be large enough to be likely to yield the desired mutations, but small enough so that the capacity of the selection system is not exceeded. This is not always possible given the size and complexity of most proteins.

SUMMARY OF THE INVENTION

This invention pertains to a method of mutagenesis for the generation of novel or improved proteins (or polypeptides) and to libraries of mutant proteins and specific mutant proteins generated by the method. The protein, peptide or polypeptide targeted for mutagenesis can be a natural, synthetic or engineered protein, peptide or polypeptide or a variant (e.g., a mutant). In one embodiment, the method comprises introducing a predetermined amino acid into each and every position in a predefined region (or several different regions) of the amino acid sequence of a protein. A protein library is generated which contains mutant proteins having the predetermined amino acid in one or more positions in the region and, collectively, in every position in the region. The method can be referred to as "walk-through" mutagenesis because, in effect, a single, predetermined amino acid is substituted position-by-position throughout a defined region of a protein. This allows for a systematic evaluation of the role of a specific amino acid in the structure or function of a protein.

The library of mutant proteins can be generated by synthesizing a single mixture of oligonucleotides which encodes all of the designed variations of the amino acid sequence for the region containing the predetermined amino acid. This mixture of oligonucleotides is synthesized by incorporating in each condensation step of the synthesis both the nucleotide of the sequence to be mutagenized (for example, the wild type sequence) and the nucleotide required for the codon of the predetermined amino acid. Where a nucleotide of the sequence to be mutagenized is the same as a nucleotide for the predetermined amino acid, no additional nucleotide is added. In the resulting mixture, oligonucleotides which contain at least one codon for the predetermined amino acid make up from about 12.5% to 100% of the constituents. In addition, the mixture of oligonucleotides encodes a statistical (in some cases Gaussian) distribution of amino acid sequences containing the predetermined amino acid in a range of no positions to all positions in the sequence.

The mixture of oligonucleotides is inserted into a gene encoding the protein to be mutagenized (such as the wild type protein) in place of the DNA encoding the region. The recombinant mutant genes are cloned in a suitable expression vector to provide an expression library of mutant proteins that can be screened for proteins that have desired properties. The library of mutant proteins produced by this oligonucleotide-mediated procedure contains a larger ratio of informative mutants (those containing the predetermined amino acid in the defined region) relative to noninformative mutants than libraries produced by methods of saturation mutagenesis. For example, preferred libraries are made up of mutants which have the predetermined amino acid in essentially each and every position in the region at a frequency ranging from about 12.5% to 100%.

This method of mutagenesis can be used to generate libraries of mutant proteins which are of a practical size for screening. The method can be used to study the role of specific amino acids in protein structure and function and to develop new or improved proteins and polypeptides such as enzymes, antibodies, binding fragments or analogues thereof, single chain antibodies and catalytic antibodies.

BRIEF DESCRIPTION OF THE FIGURES

FIGS. 3A-3C illustrates the design of "degenerate" oligonucleotides for walk-through mutagenesis of the CDR1 (FIG. 3a) and CDR3 (FIG. 3b) of the heavy chain, and CDR2 (FIG. 3c) of the light chain of MCPC 603.

FIGS. 4A-4B illustrates the design of a "window" of mutagenesis, and shows the sequences of degenerate oligonucleotides for mutation of CDR3 of the heavy chain (FIG. 4a) and CDR2 of the light chain of MCPC 603 (FIG. 4b).

FIGS. 5a and 5b illustrate the design of "windows" of mutagenesis and show the sequences of degenerate oligonucleotides for two different wlk-through mutagenesis procedures with His in CDR2 of the heavy chain of MCPC 603.

FIG. 6 illustrates the design and sequences of degenerate oligonucleotides for walk-through mutagenesis of CDR2 of the heavy chain of MCPC 603.

FIG. 7 illustrates a "window" of mutagenesis in the HIV protease, consisting of three consecutive amino acid residues at the catalytic site. The design and sequences of degenerate oligonucleotides for three rounds of walk-through mutagenesis of the region with Asp, Ser and His is shown.

FIGS. 8A-8E illustrates the design and sequence of degenerate oligonucleotides for walk-through mutagenesis of five CDRs of MCPC 603. The degenerate oligonucleotides for walk-through mutagenesis of the CDR1 (FIG. 8a) and CDR3 (FIG. 8b) of the light chain, and of CDR 1 (FIG. 8c), CDR2 (FIG. 8d), and CDR3 (FIG. 8e) of the heavy chain are shown.

DETAILED DESCRIPTION OF THE INVENTION

The study of proteins has revealed that certain amino acids play a crucial role in their structure and function. For example, it appears that only a discrete number of amino acids participate in the catalytic event of an enzyme. Serine proteases are a family of enzymes present in virtually all organisms, which have evolved a structurally similar catalytic site characterized by the combined presence of serine, histidine and aspartic acid. These amino acids form a catalytic triad which, possibly along with other determinants, stabilizes the transition state of the substrate. The functional role of this catalytic triad has been confirmed by individual and by multiple substitutions of serine, histidine and aspartic acid by site-directed mutagenesis of serine proteases and the importance of the interplay between these amino acid residues in catalysis is now well established. These same three amino acids are involved in the enzymatic mechanism of certain lipases as well. Similarly, a large number of other types of enzymes are characterized by the peculiar conformation of their catalytic site and the presence of certain kinds of amino acid residues in the site that are primarily responsible for the catalytic event. For an extensive review, see *Enzyme Structure and Mechanism*, 1985, by A. Fersht, Freeman Ed., New York.

Though it is clear that certain amino acids are critical to the mechanism of catalysis, it is difficult, if not impossible, to predict which position (or positions) an amino acid must occupy to produce a functional site such as a catalytic site. Unfortunately, the complex spatial configuration of amino acid side chains in proteins and the interrelationship of different side chains in the catalytic pocket of enzymes are insufficiently understood to allow for such predictions. As pointed out above, selective (site-directed) mutagenesis and saturation mutagenesis are of limited utility for the study of protein structure and function in view of the enormous number of possible variations in complex proteins.

The method of this invention provides a systematic and practical approach for evaluating the importance of particular amino acids, and their position within a defined region of a protein, to the structure or function of a protein and for producing useful proteins. The method begins with the assumption that a certain, predetermined amino acid is important to a particular structure or function. The assumption can be based on a mere guess. More likely, the assumption is based upon what is known about the amino acid from the study of other proteins. For example, the amino acid can be one which has a role in catalysis, binding or another function.

Figure 1:
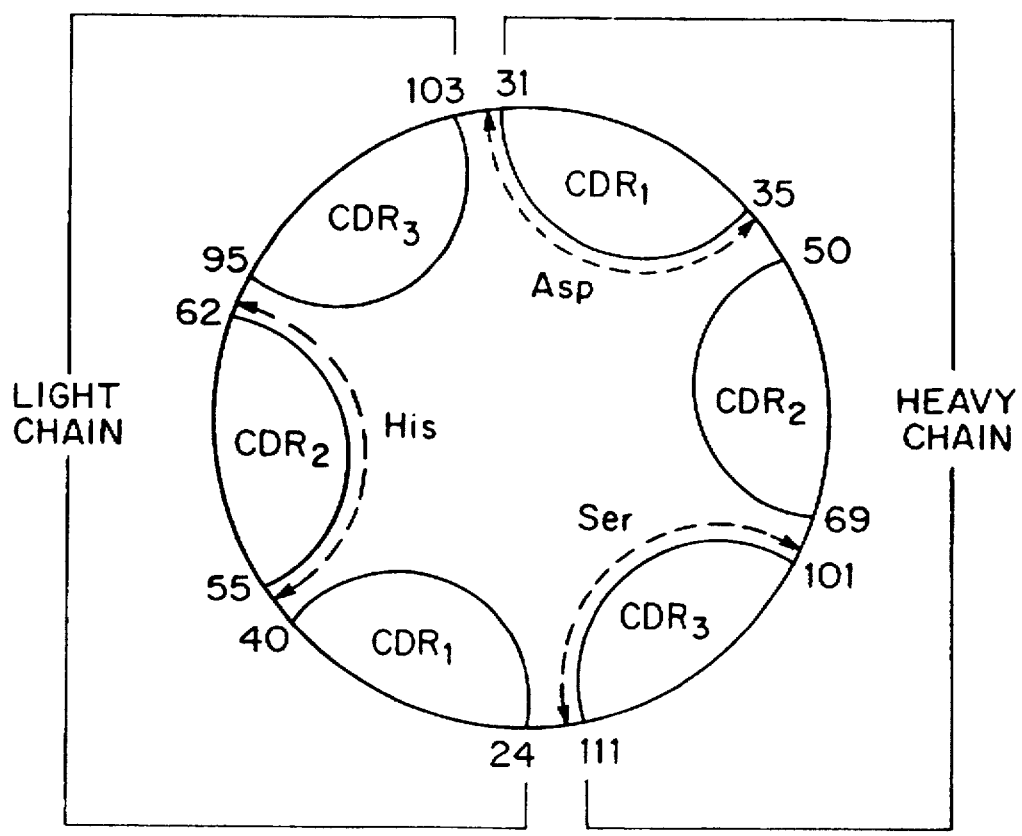
FIG. 1 is a schematic depiction a "walk-through" mutagenesis of the Fv region of immunoglobulin MCPC 603, performed for the CDR1 (Asp) and CDR3 (Ser) of the heavy(H) chain and CDR2 (His) of the light chain (L).
Figure 2:
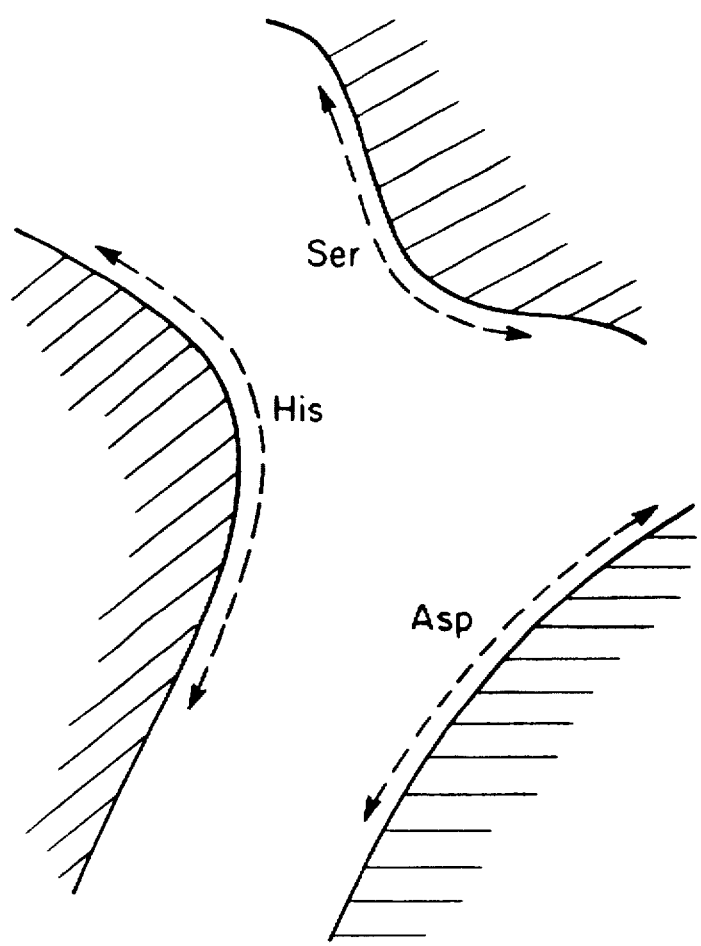
FIG. 2 is a schematic depiction of a "walk-through" mutagenesis of an enzyme active site; three amino acid regions of the active site are substituted in each and every position with amino acids of a serine-protease catalytic triad.

With selection of the predetermined amino acid, a library of mutants of the protein to be studied is generated by incorporating the predetermined amino acid into each and every position of the region of the protein. As schematically depicted in FIGS. 1 and 2, the amino acid is substituted in or "walked-through" all (or essentially all) positions of the region.

The library of mutant proteins contains individual proteins which have the predetermined amino acid in each and every position in the region. The protein library will have a higher proportion of mutants that contain the predetermined amino acid in the region (relative to mutants that do not), as compared to libraries that would be generated by completely random mutation, such as saturation mutation. Thus, the desired types of mutants are concentrated in the library. This is important because it allows more and larger regions of proteins to be mutagenized by the walk-through process, while still yielding libraries of a size which can be screened. Further, if the initial assumption is correct and the amino acid is important to the structure or function of the protein, then the library will have a higher proportion of informative mutants than a library generated by random mutation.

In another embodiment, a predetermined amino acid is introduced into each of certain selected positions witin a predefined region or regions. Certain selected positions may be known or thought to be more promising due to structural constraints. Such considerations, based on structural information or modeling of the molecule mutagenized and/or the desired structure, can be used to select a subset of positions within a region or regions for mutagenesis. Thus, the amino acids mutagenized within a region need not be contiguous. Walking an amino acid through certain selected positions in a region can minimize the number of variants produced.

The size of a library will vary depending upon the length and number of regions and amino acids within a region that are mutagenized. Preferably, the library will be designed to contain less than $10^{10}$ mutants, and more preferably less than $10^9$ mutants.

In a preferred embodiment, the library of mutant proteins is generated by synthesizing a mixture of oligonucleotides (a degenerate oligonucleotide) encoding selected permutations of amino acid sequences for the defined region of the protein. Conveniently, the mixture of oligonucleotides can be produced in a single synthesis. This is accomplished by incorporating, at each position within the oligonucleotide, both a nucleotide required for synthesis of the wild-type protein (or other protein to be mutagenized) and a single appropriate nucleotide required for a codon of the predetermined amino acid. (This differs from the oligonucleotides produced in saturation mutagenesis in that, for each DNA position mutagenized, only a single additional nucleotide, as opposed to three for "saturation", is added). The two nucleotides are typically, but not necessarily, used in approximately equal concentrations for the reaction so that there is an equal chance of incorporating either one into the sequence at the position. When the nucleotide of the wild type sequence and the nucleotide for the codon of the predetermined amino acid are the same, no additional nucleotide is incorporated.

Depending upon the number of nucleotides that are mutated to provide a codon for a predetermined amino acid, the mixture of oligonucleotides will generate a limited number of new codons. For example, if only one nucleotide is mutated, the resulting DNA mixture will encode either the original codon or the codon of the predetermined amino acid. In this case, 50% of all oligonucleotides in the resulting mixture will contain the codon for the predetermined amino acid at that position. If two nucleotides are mutated in any combination (first and second, first and third or second and third), four different codons are possible and at least one will encode the predetermined amino acid, a 25% frequency. If all three bases are mutated, then the mixture will produce eight distinct codons, one of which will encode the predetermined amino acid. Therefore the codon will appear in the position with a minimum frequency of 12.5%. However, it is likely that an additional one of the eight codons would code for the same amino acid and/or a stop codon and accordingly, the frequency of predetermined amino acid would be greater than 12.5%.

By this method, a mixture of oligonucleotides is produced having a high proportion of sequences containing a codon for the predetermined amino acid. Other restrictions in the synthesis can be imposed to increase this proportion (by reducing the number of oligonucleotides in the mixture that do not contain at least one codon for the predetermined amino acid). For example, when a complete codon (three nucleotides) must be substituted to arrive at the codon for the predetermined amino acid, the substitute nucleotides only may be introduced (so that the codon for the predetermined amino acid appears with 100% frequency at the position). The proportions of the wild type nucleotide and the nucleotide coding for the preselected amino acid may be adjusted at any or all positions to influence the proportions of the encoded amino acids.

In a protein library produced by this procedure, the proportion of mutants which have at least one residue of the predetermined amino acid in the defined region ranges from about 12.5% to 100% of all mutants in the library (assuming approximately equal proportions of wild type bases and preselected amino acid bases are used in the synthesis). Typically, the proportion ranges from about 25% to 50%.

The libraries of protein mutants will contain a number equal to or smaller than $2^n$, where n represents the number of nucleotides mutated within the DNA encoding the protein region. Because there can be only a limited number of changes for each codon (one, two or three) the number of protein mutants will range from $2^m$ to $8^m$, where m is the number of amino acids that are mutated within that region. This represents a dramatic reduction compared with the $19^m$ mutants generated by a saturation mutagenesis. For instance, for a protein region of seven amino acids, the number of mutants generated by a walk-through mutagenesis (of one amino acid) would result in a 0.000014% to 0.24% fraction of the number of mutants that would be generated by saturation mutagenesis of the region, a very significant reduction.

An additional, advantageous characteristic of the library generated by this method is that the proteins which contain the predetermined amino acid conform to a statistical distribution with respect to the number of residues of the amino acid in the amino acid sequence. Accordingly, the sequences range from those in which the predetermined amino acid does not appear at any position in the region to those in which the predetermined amino acid appears in every position in the region. Thus, in addition to providing a means for systematic insertion of an amino acid into a region of a protein, this method provides a way to enrich a region of a protein with a particular amino acid. This enrichment could lead to enhancement of an activity attributable to the amino acid or to entirely new activities.

The mixture of oligonucleotides for generation of the library can be synthesized readily by known methods for DNA synthesis. The preferred method involves use of solid phase beta-cyanoethyl phosphoramidite chemistry. See U.S. Pat. No. 4,725,677. For convenience, an instrument for automated DNA synthesis can be used containing ten reagent vessels of nucleotide synthons (reagents for DNA synthesis), four vessels containing one of the four synthons (A, T, C and G) and six vessels containing mixtures of two synthons (A+T, A+C, A+G, T+C, T+G and C+G).

The wild type nucleotide sequence can be adjusted during synthesis to simplify the mixture of oligonucleotides and minimize the number of amino acids encoded. For example, if the wild type amino acid is threonine (ACT), and the preselected amino acid is arginine (AGA or AGG), two base changes are required to encode arginine, and three amino acids are produced (e.g., AGA, Arg; AGT, Ser; ACA, ACT Thr). By changing the wild type nucleotide sequence to ACA or ACG, only a single base change would be required to encode arginine. Thus, if ACG were chosen to encode the wild type threonine instead of ACT, only the central base would need to be changed to G to obtain arginine, and only arginine and threonine would be produced at that position. Depending on the particular codon and the identity of the preselected amino acid, similar adjustments at any position of the wild type codon may reduce the number of variants generated.

The mixture of oligonucleotides is inserted into a cloned gene of the protein being mutagenized in place of the nucleotide sequence encoding the amino acid sequence of the region to produce recombinant mutant genes encoding the mutant proteins. To facilitate this, the mixture of oligonucleotides can be made to contain flanking recognition sites for restriction enzymes. See Crea, R., U.S. Pat. No. 4,888,286. The recognition sites are designed to correspond to recognition sites which either exist naturally or are introduced in the gene proximate to the DNA encoding the region. After conversion into double stranded form, the oligonucleotides are ligated into the gene by standard techniques. By means of an appropriate vector, the genes are introduced into a host cell suitable for expression of the mutant proteins. See e.g., Huse, W. D. et al., *Science* 246: 1275 (1989); Viera, J. et al., *Meth. Enzymol.* 153: 3 (1987).

In fact, the degenerate oligonucleotides can be introduced into the gene by any suitable method, using techniques well-known in the art. In cases where the amino acid sequence of the protein to be mutagenized is known or where the DNA sequence is known, gene synthesis is a possible approach (see e.g., Alvarado-Urbina, G. et al., *Biochem. Cell. Biol.* 64: 548–555 (1986); Jones et al., *Nature* 321: 522 (1986)). For example, partially overlapping oligonucleotides, typically about 20–60 nucleotides in length, can be designed. The internal oligonucleotides (B through G and I through O) are phosphorylated using T4 polynucleotide kinase to provide a 5' phosphate group. Each of the oligonucleotides can be annealed to their complementary partner to give a double-stranded DNA molecule with single-stranded extensions useful for further annealing. The annealed pairs can then be mixed together and ligated to form a full length double-stranded molecule:

A  B  C  D  E  F  G  H
―  ―  ―  ―  ―  ―  ―  ―
 T  J  K  L  M  N  O  P

Convenient restriction sites can be designed near the ends of the synthetic gene for cloning into a suitable vector. The full length molecules can be cleaved with those restriction enzymes, gel purified, electroeluted and ligated into a suitable vector. Convenient restriction sites can also be incorporated into the sequence of the synthetic gene to facilitate introduction of mutagenic cassettes.

As an alternative to synthesizing oligonucleotides representing the full-length double-stranded gene, oligonucleotides which partially overlap at their 3' ends (i.e., with complementary 3' ends) can be assembled into a gapped structure and then filled in with the Klenow fragment of DNA polymerase and deoxynucleotide triphosphates to make a full length double-stranded gene. Typically, the overlapping oligonucleotides are from 40–90 nucleotides in length. The extended oligonucleotides are then ligated using T4 ligase. Convenient restriction sites can be introduced at the ends and/or internally for cloning purposes. Following digestion with an appropriate restriction enzyme or enzymes, the gene fragment is gel-purified and ligated into a suitable vector. Alternatively, the gene fragment could be blunt end ligated into an appropriate vector.

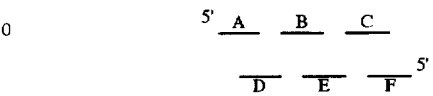

In these approaches, if convenient restriction sites are available (naturally or engineered) following gene assembly, the degenerate oligonucleotides can be introduced subsequently by cloning the cassette into an appropriate vector. Alternatively, the degenerate oligonucleotides can be incorporated at the stage of gene assembly. For example, when both strands of the gene are fully chemically synthesized, overlapping and complementary degenerate oligonucleotides can be produced. Complementary pairs will anneal with each other. An example of this approach is illustrated in Example 1.

When partially overlapping oligos are used in the gene assembly, a set of degenerate nucleotides can also be directly incorporated in place of one of the oligos. The appropriate complementary strand is synthesized during the extension reaction from a partially complementary oligo from the other strand by enzymatic extension with the Klenow fragment of DNA polymerase, for example. Incorporation of the degenerate oligonucleotides at the stage of synthesis also simplifies cloning where more than one domain of a gene is mutagenized.

In another approach, the gene of interest is present on a single stranded plasmid. For example, the gene can be cloned into an M13 phage vector or a vector with a filamentous phage origin of replication which allows propagation of single-stranded molecules with the use of a helper phage. The single-stranded template can be annealed with a set of degenerate probes. The probes can be elongated and ligated, thus incorporating each variant strand into a population of molecules which can be introduced into an appropriate host (Sayers, J. R. et al., *Nucleic Acids Res.* 16: 791–802 (1988)). This approach can circumvent multiple cloning steps where multiple domains are selected for mutagenesis.

Polymerase chain reaction (PCR) methodology can also be used to incorporate degenerate oligonucleotides into a gene. For example, the degenerate oligonucleotides themselves can be used as primers for extension.

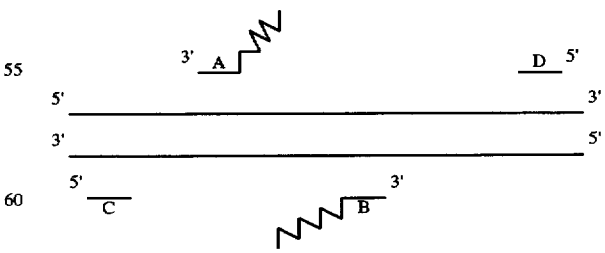

In this embodiment, A and B are populations of degenerate oligonucleotides encoding the mutagenic cassettes or "windows", and the windows are complementary to each other (the zig-zag portion of the oligos represents the degenerate portion). A and B also contain wild type sequences complementary to the template on the 3' end for amplification and are thus primers for amplification capable of generating fragments incorporating a window. C and D are oligonucleotides which can amplify the entire gene or region of interest, including those with mutagenic windows incorporated (Steffan, N. H. et al., *Gene* 77: 51–59 (1989)). The extension products primed from A and B can hybridize through their complementary windows and provide a template for production of full-length molecules using C and D as primers. C and D can be designed to contain convenient sites for cloning. The amplified fragments can then be cloned.

Libraries of mutants generated by any of the above techniques or other suitable techniques can be screened to identify mutants of desired structure or activity. The screening can be done by any appropriate means. For example, catalytic activity can be ascertained by suitable assays for substrate conversion and binding activity can be evaluated by standard immunoassay and/or affinity chromatography.

The method of this invention can be used to mutagenize any region of a protein, protein subunit or polypeptide. The description heretofore has centered around proteins, but it should be understood that the method applies to polypeptides and multi-subunit proteins as well. The regions mutagenized by the method of this invention can be continuous or discontinuous and will generally range in length from about 3 to about 30 amino acids, typically 5 to 20 amino acids.

Usually, the region studied will be a functional domain of the protein such as a binding or catalytic domain. For example, the region can be the hypervariable region (complementarity-determining region or CDR) of an immunoglobulin, the catalytic site of an enzyme, or a binding domain.

As mentioned, the amino acid chosen for the "walk through" mutagenesis is generally selected from those known or thought to be involved in the structure or function of interest. The twenty naturally occurring amino acids differ only with respect to their side chain. Each side chain is reponsible for chemical properties that make each amino acid unique. For review, see *Principles of Protein Structure*, 1988, by G. E. Schulz and R. M. Schirner, Springer-Verlag.

From the chemical properties of the side chains, it appears that only a selected number of natural amino acids preferentially participate in a catalytic event. These amino acids belong to the group of polar and neutral amino acids such as Ser, Thr, Asn, Gln, Tyr, and Cys, the group of charged amino acids, Asp and Glu, Lys and Arg, and especially the amino acid His.

Typical polar and neutral side chains are those of Cys, Ser, Thr, Asn, Gln and Tyr. Gly is also considered to be a borderline member of this group. Ser and Thr play an important role in forming hydrogen-bonds. Thr has an additional asymmetry at the beta carbon, therefore only one of the stereoisomers is used. The acid amide Gln and Asn can also form hydrogen bonds, the amido groups functioning as hydrogen donors and the carbonyl groups functioning as acceptors. Gln has one more $CH_2$ group than Asn which renders the polar group more flexible and reduces its interaction with the main chain. Tyr has a very polar hydroxyl group (phenolic OH) that can dissociate at high pH values. Tyr behaves somewhat like a charged side chain; its hydrogen bonds are rather strong.

Neutral polar acids are found at the surface as well as inside protein molecules. As internal residues, they usually form hydrogen bonds with each other or with the polypeptide backbone. Cys can form disulfide bridges.

Histidine (His) has a heterocyclic aromatic side chain with a pK value of 6.0. In the physiological pH range, its imidazole ring can be either uncharged or charged, after taking up a hydrogen ion from the solution. Since these two states are readily available, His is quite suitable for catalyzing chemical reactions. It is found in most of the active centers of enzymes.

Asp and Glu are negatively charged at physiological pH. Because of their short side chain, the carboxyl group of Asp is rather rigid with respect to the main chain. This may be the reason why the carboxyl group in many catalytic sites is provided by Asp and not by Glu. Charged acids are generally found at the surface of a protein.

In addition, Lys and Arg are found at the surface. They have long and flexible side chains. Wobbling in the surrounding solution, they increase the solubility of the protein globule. In several cases, Lys and Arg take part in forming internal salt bridges or they help in catalysis. Because of their exposure at the surface of the proteins, Lys is a residue more frequently attacked by enzymes which either modify the side chain or cleave the peptide chain at the carbonyl end of Lys residues.

For the purpose of introducing catalytically important amino acids into a region, the invention preferentially relates to a mutagenesis in which the predetermined amino acid is one of the following group of amino acids: Ser, Thr, Asn, Gln, Tyr, Cys, His, Glu, Asp, Lys, and Arg. However, for the purpose of altering binding or creating new binding affinities, any of the twenty naturally occurring amino acids can be selected.

Importantly, several different regions or domains of a protein can be mutagenized simultaneously. The same or a different amino acid can be "walked-through" each region. This enables the evaluation of amino acid substitutions in conformationally related regions such as the regions which, upon folding of the protein, are associated to make up a functional site such as the catalytic site of an enzyme or the binding site of an antibody. This method provides a way to create modified or completely new catalytic sites. As depicted in FIG. 1, the six hypervariable regions of an immunoglobulin, which make up the unique aspects of the antigen binding site (Fv region), can be mutagenized simultaneously, or separately within the $V_H$ or $V_L$ chains, to study the three dimensional interrelationship of selected amino acids in this site.

The method of this invention opens up new possibilities for the design of many different types of proteins. The method can be used to improve upon an existing structure or function of a protein. For example, the introduction of additional "catalytically important" amino acids into a catalytic domain of an enzyme may result in enhanced catalytic activity toward the same substrate. Alternatively, entirely new structures, specificities or activities may be introduced into a protein. De novo synthesis of enzymatic activity can be achieved as well. The new structures can be built on the natural "scaffold" of an existing protein by mutating only relevant regions by the method of this invention.

The method of this invention is especially useful for modifying antibody molecules. As used herein, antibody molecules or antibodies refers to antibodies or portions thereof, such as full-length antibodies, Fv molecules, or other antibody fragments, individual chains or fragments thereof (e.g., a single chain of Fv), single chain antibodies, and chimeric antibodies. Alterations can be introduced into the variable region and/or into the framework (constant) region of an antibody. Modification of the variable region can produce antibodies with better antigen binding properties, and catalytic properties. Modification of the framework region could lead to the improvement of chemophysical properties, such as solubility or stability, which would be useful, for example, in commercial production. Typically, the mutagenesis will target the Fv region of the immunoglobulin molecule—the structure responsible for antigen-binding activity which is made up of variable regions of two chains, one from the heavy chain ($V_H$) and one from the light chain ($V_L$).

The method of this invention is suited to the design of catalytic proteins, particularly catalytic antibodies. Presently, catalytic antibodies can be prepared by an adaptation of standard somatic cell fusion techniques. In this process, an animal is immunized with an antigen that resembles the transition state of the desired substrate to induce production of an antibody that binds the transition state and catalyzes the reaction. Antibody-producing cells are harvested from the animal and fused with an immortalizing cell to produce hybrid cells. These cells are then screened for secretion of an antibody that catalyzes the reaction. This process is dependent upon the availability of analogues of the transition state of a substrate. The process may be limited because such analogues are likely to be difficult to identify or synthesize in most cases.

The method of this invention provides a different approach which eliminates the need for a transition state analogue. By the method of this invention, an antibody can be made catalytic by the introduction of suitable amino acids into the binding site of an immunoglobulin (Fv region). The antigen-binding site (Fv) region is made-up of six hypervariable (CDR) loops, three derived from the immunoglobulin heavy chain (H) and three from the light chain (L), which connect beta strands within each subunit. The amino acid residues of the CDR loops contribute almost entirely to the binding characteristics of each specific monoclonal antibody. For instance, catalytic triads modeled after serine proteases can be created in the hypervariable segments of the Fv region of an antibody and screened for proteolytic activity.

The method of this invention can be used to produce many different enzymes or catalytic antibodies, including oxidoreductases, transferases, hydrolases, lyases, isomerases and ligases. Among these classes, of particular importance will be the production of improved proteases, carbohydrases, lipases, dioxygenases and peroxidases. These and other enzymes that can be prepared by the method of this invention have important commercial applications for enzymatic conversions in health care, cosmetics, foods, brewing, detergents, environment (e.g., wastewater treatment), agriculture, tanning, textiles, and other chemical processes. These include, but are not limited to, diagnostic and therapeutic applications, conversions of fats, carbohydrates and protein, degradation of organic pollutants and synthesis of chemicals. For example, therapeutically effective proteases with fibrinolytic activity, or activity against viral structures necessary for infectivity, such as viral coat proteins, could be engineered. Such proteases could be useful anti-thrombotic agents or anti-viral agents against viruses such as AIDS, rhinoviruses, influenza, or hepatitis. In the case of oxygenases (e.g., dioxygenases), a class of enzymes requiring a co-factor for oxidation of aromatic rings and other double bonds, industrial applications in biopulping processes, conversion of biomass into fuels or other chemicals, conversion of waste water contaminants, bioprocessing of coal, and detoxification of hazardous organic compounds are possible applications of novel proteins.

Assays for these activities can be designed in which a cell requires the desired activity for growth. For example, in screening for activites that degrade toxic compounds, the incorporation of lethal levels of the the toxic compound into nutrient plates would permit the growth only of cells expressing an activity which degrades the toxic compound (Wasserfallen, A., Rekik, M., and Harayama, S., *Biotechnology* 9: 296–298 (1991)). Alternatively, in screening for an enzyme that uses a non-toxic substrate, it is possible to use that substrate as the sole carbon source or sole source of another appropriate nutrient. In this case also, only cells expressing the enzyme activity will grow on the plates. In these methods, it is not necessary that the enzyme activity be secreted if the substrate or a product of the substrate (converted extracellularly by another activity) can be taken up by the cell. In addition, one can test directly for a novel function by incorporating a substrate into the medium which when acted upon leads to a visual indication of activity.

Illustrations of Walk-through Mutagenesis

Model I

To further illustrate the invention, a "walkthrough" mutagenesis of three of the hypervariable regions or complemetarity determining regions (CDRs) of the monoclonal antibody MCPC 603 is described. CDR1 and CDR3 of the heavy chain (VH) and CDR2 of the light chain region (VL) were the domains selected for walk-through mutagenesis. For this embodiment, the amino acids selected are the three residues of the catalytic triad of serine proteases, Asp, His and Ser. Asp was selected for VH CDR1, Ser was selected for VH CDR3, and His was selected for VL CDR2.

MCPC 603 is a monoclonal antibody that binds phosphorylcholine. This immunoglobulin is recognized as a good model for investigating binding and catalysis because the protein and its binding region have been well characterized structurally. The CDRs for the MCPC 603 antibody have been identified. In the heavy chain, CDR1 spans amino acids 31–35, CDR2 spans 50–69, and CDR3 spans 101–111. In the light chain, the amino acids of CDR1 are 24–40, CDR2 spans amino acids 55–62, and CDR3 spans amino acids 95–103. The amino acid numbers in the Figures correspond to the numbers of the amino acids in the parent MCPC 603 molecule.

The cDNA corresponding to an immunoglobulin variable region can be directly cloned and sequenced without constructing cDNA libraries. Because immunoglobulin variable regions genes are flanked by conserved sequences, a polymerase chain reaction (PCR) can be used to amplify, clone and sequence both the light and heavy chain genes from a small number of hybridoma cells with the use of consensus 5' and 3' primers. See Chiang, Y. L. et al., *BioTechniques* 7: 360 (1989). Furthermore, the DNA coding for the amino acids flanking the CDR regions can be mutagenized by site directed mutagenesis to generate restriction enzyme recognition sites useful for further "cassette" mutagenesis. See U.S. Pat. No. 4,888,286, supra. To facilitate insertion of the degenerate oligonucleotides, the mixture is synthesized to contain flanking recognition sites for the same restriction enzymes. The degenerate mixture can be first converted into double stranded DNA by enzymatic methods (Oliphant, A. R. et al., *Gene* 44: 177 (1986)) and then inserted into the gene of the region to be mutagenized in place of the CDR nucleotide sequence encoding the naturally-occurring (wild type) amino acid sequence.

Alternatively, one of the other approaches described above, such as a gene synthesis approach, could be used to make a library of plasmids encoding variants in the desired regions. The published amino acid sequence of the MCPC 603 VH and VL regions can be converted to a DNA sequence. (Rudikoff, S. and Potter, M., *Biochemistry* 13: 4033 (1974)). Note that the wild type DNA sequence of MCPC 603 has also been published (Pluckthun, A. et al., *Cold Spring Harbor Symp. Quant. Biol.*, Vol. LII: 105–112 (1987)). Restriction sites can be incorporated into the sequence to facilitate introduction of degenerate oligonucleotides or the degenerate sequences may be introduced at the stage of gene assembly.

The design of the oligonucleotides for walk-through mutagenesis in the CDRs of MCPC 603 is shown in FIG. 3. In each case, the positions or "windows" to be mutagenized are shown. It is understood that the oligonucleotide synthesized can be larger than the window shown to facilitate insertion into the target construct. The mixture of oligonucleotides corresponding to the VH CDR1 is designed in which each amino acid of the wild type sequence is substituted by Asp (FIG. 3a). Two codons specify asp (GAC and GAT). The first codon of CDR1 does not require any substitution. The second codon (TTC, Phe) requires substitution at the first (T to G) and second position (T to A) in order to convert it into a codon for Asp. The third codon (TAC, Tyr) requires only one substitution at the first position (T to G). The fourth codon (ATG, Met) requires three substitutions, the first being A to G, the second T to A and the third G to T. The fifth codon (GAG, Glu) requires only one substitution at the third position (G to T). The resulting mixture of oligonucleotides is depicted below.

This represents a mixture of $2^7=128$ different oligonucleotide sequences.

From the genetic code, it is possible to deduce all the amino acids that will substitute the original amino acid in each position. For this case, the first amino acid will always be Asp (100%), the second will be Phe (25%), Asp (25%), Tyr (25%) or Val (25%), the third amino acid will be Tyr (50%) or Asp (50%); the fourth will be Met (12.5%), Asp (12.5%), Val (25%), Glu (12.5%), Asn (12.5%), Ile (12.5%) or Lys (12.5%); and the fifth codon will be either Glu (50%) or Asp (50%). In total, 128 oligonucleotides which will code for 112 different protein sequences ($1\times4\times2\times7\times2=112$) are generated. Among the 112 different amino acid sequences generated will be the wild type sequence (which has an Asp residue at position 31), and sequences differing from wild type in that they contain from one to four Asp residues at positions 32–35, in all possible permutations (see FIG. 3a). In addition, some sequences, either with or without Asp substitutions, will contain an amino acid-neither wild type nor Asp- at positions 32, 34 or both. These amino acids are introduced by permutations of the nucleotides which encode the wild type amino acid and the preselected amino acid. For example, in FIG. 3a, at position 32, tyrosine (Tyr) and valine (Val) are generated in addition to the wild type phenylalanine (Phe) residue and the preselected Asp residue.

The CDR3 of the VH region of MCPC603 is made up of 11 amino acids, as shown in FIG. 3b. A mixture of oligonucleotides is designed in which each non-serine amino acid of the wild type sequence is replaced by serine (Ser), as described above for CDR1. Six codons (TCX and AGC, AGT) specify Ser. The substitutions required throughout the wild-type sequence amount to 12. As a result, the oligonucleotide mixture produced contains $2^{12}=4096$ different oligonucleotides which, in this case, will code for 4096 protein sequences. Among these sequences will be some containing a single serine residue (in addition to the serine 105) in any one of the other positions (101–104, 106–111), as well as variants with more than one serine, in any combination (see FIG. 3b).

The CDR2 of the VL region of MCPC603 contains eight amino acids (56–63). Seven of these amino acids (56–62) were selected for walk-through mutagenesis as depicted in FIG. 3c. The mixture of oligonucleotides is designed in which each amino acid of the wild type sequence will be replaced by histidine (His). Two codons (CAT and CAC) specify His. The substitutions required throughout the wild-type DNA sequence total 13. Thus, the oligonucleotide mixture produced contains $2=8192$ oligonucleotides which specify 8192 different peptide sequences (see FIG. 3c).

As result of this mutagenesis method, by the synthesis and the use of three oligonucleotide mixtures, a library of Fv sequences can be produced which contains $112\times4096\times8192=3.76\times10^9$ different protein sequences. A significant proportion of these sequences will encode the amino acid triad His, Ser, Asp typical of serine proteases within the hypervariable regions.

The synthesis of the degenerate mixture of oligonucleotides can be conveniently obtained in an automated DNA synthesizer programmed to deliver either one nucleotide to the reaction chamber or a mixture of two nucleotides in equal ratio, mixed prior to the delivery to reaction chamber. An alternative synthetic procedure would involve premixing two different nucleotides in a reagent vessel. A total of 10 reagent vessels, four of which containing the individual bases and the remaining 6 containing all of the possible two base mixtures among the 4 bases, can be employed to synthesize any mixture of oligonucleotides for this mutagenesis process. For example, the DNA synthesizer can be designed to contain the following ten chambers:

| Chamber | Synthon |
| --- | --- |
| 1 | A |
| 2 | T |
| 3 | C |
| 4 | G |
| 5 | (A + T) |
| 6 | (A + C) |
| 7 | (A + G) |
| 8 | (T + C) |
| 9 | (T + G) |
| 10 | (C + G) |

With this arrangement, any nucleotide can be replaced by a combination of two nucleotides at any position of the sequence.

The following sequence of reactions is required to synthesize the desired mixture of degenerate oligonucleotides for:

| | |
| --- | --- |
| VH CDR1: | 4, 1, 3, 9, 5, 3, 9, 1, 3, 7, 5, 9, 4, 1, 9 |
| VH CDR3: | 1, 7, 3, 2, 6, 3, 2, 6, 3, 7, 4, 3, 1, 4, 3, 1, 10, 2, 2, 10, 4, 2, 6, 3, 2, 8, 3, 9, 6, 3, 9, 8, 2 |
| VL CDR2: | 10, 7, 2, 10, 6, 2, 6, 7, 3, 6, 6, 3, 3, 7, 2, 10, 1, 5, 8, 6, 2 |

As an alternative to this procedure, if mixing of individual bases in the lines of the oligonucleotide synthesizer is possible, the machine can be programmed to draw from two or more reservoirs of pure bases to generate the desired proportion of nucleotides.

Each mixture of synthetic oligonucleotides can be inserted into the gene for the respective MCPC 603 variable region. The oligonucleotides can be converted into double-stranded chains by enzymatic techniques (see e.g., Oliphant, A. R. et al., 1986, supra) and then ligated into a restricted plasmid containing the gene coding for the protein to be mutagenized. The restriction sites could be naturally occurring sites or engineered restriction sites.

The mutant MCPC 603 genes constructed by these or other suitable procedures described above can be expressed in a convenient *E. coli* expression system, such as that described by Pluckthun and Skerra. (Pluckthun, A. and Skerra, A., *Meth. Enzymol.* 178: 476–515 (1989); Skerra, A. et al., *Biotechnology* 9: 273–278 (1991)). The mutant proteins can be expressed for secretion in the medium and/or in the cytoplasm of the bacteria, as described by M. Better and A. Horwitz, *Meth. Enzymol.* 178: 476 (1989).

These and other Fv variants, or antibody variants produced by the present method can also be produced in other microorganisms such as yeast, or in mammalian cells, such as myeloma or hybridoma cells. The Fv variants can be produced as individual VH and VL fragments, as single chains (see Huston, J. S. et al., *Proc. Natl. Acad. Sci. USA* 85: 5879–5883 (1988)), as parts of larger molecules such as Fab, or as entire antibody molecules.

In a preferred embodiment, the single domains encoding VH and VL are each attached to the 3' end of a sequence encoding a signal sequence, such as the ompA, phoA or pelB signal sequence (Lei, S. P. et al., *J. Bacteriol.* 169: 4379 (1987)). These gene fusions are assembled in a dicistronic construct, so that they can be expressed from a single vector, and secreted into the periplasmic space of *E. coli* where they will refold and can be recovered in active form. (Skerra, A. et al., *Biotechnology* 9: 273–278 (1991)). The mutant VH genes can be concurrently expressed with wild-type VL to produce Fv variants, or as described, with mutagenized VL to further increase the number and structural variety of the protein mutants.

Screening of these variants for acquisition of a proteolytic function can be accomplished in an assay as described below for the HIV protease variants (see also Example 4). Note also that since the catalytic triad of Asp-His-Ser has also been implicated in the mechanism of certain lipases, variants with lipase function may also be generated.

Model II

In a second model designed to generate a serine protease in the MCPC 603 Fv structure, Asp is selected for VH CDR1, His for VH CDR3, and Ser for VL CDR2. In this case, the degenerate oligonucleotides designed for the VH CDR1 Asp walk-through from model 1 can be reused, illustrating the interchangeable nature of the walk-through cassettes (FIG. 3a).

For the His walk-through of VH CDR3, His the nucleotides required to specify histidine codons are introduced from positions 101–111 of the VH region. FIG. 4a illustrates this walk-through procedure. Note that in this and other examples, the percentages of His produced are calculated for the case where approximately equal proportions of the wild-type or His nucleotide are introduced. These proportions can be adjusted to influence the frequency with which various amino acids are produced.

FIG. 4b illustrates the Ser walk-through of VL CDR2 in each position (55–62). Here, the sequence at positions 58 and 62 is unchanged as serine is present in the wild type sequence. Note that at position 61, although four different nucleotide sequences are generated, only three different protein sequences would be produced. This outcome is due to the fact that TAA codes for a stop codon.

Application of the method in this case can produce a library of Fv sequences which contains 112 ×196,608×96= 2.11×10$^9$ different protein sequences. Again, a significant proportion of these sequences will encode the catalytic Asp-His-Ser triad in the hypervariable regions.

Note that once a series of cassettes for a number of regions is designed, the series may be used in any permutation desired. For example, degenerate oligonucleotides may be designed for the CDRs, and these may be used together in any combination of regions and chains desired, as well as in different structures (e.g., single VL or VH chains, Fv molecules, single chain antibodies, full-size antibodies or chimeric antibodies).

Model III

In another approach to the design of a serine protease, only the heavy chain of the Fv molecule is used. Monomeric VH domains, known as single domain antibodies, with good antigen-binding affinities have been prepared (Ward, E. S. et al., *Nature* 341: 544–546 (1989)). Thus, a single VH chain can provide a scaffold for walk-through mutagenesis. For this model, Asp was selected for VH CDR1 (FIG. 3a), His for VH CDR2 and Ser for VH CDR3 (FIG. 3b). Again, two of the degenerate nucleotide sequences described in Model I can be reused (FIGS. 3a and 3b). FIG. 5a shows the His walk-through in a portion of VH CDR2.

Oligonucleotides comprising the windows shown in FIGS. 3a, 3b and FIG. 5a and degenerate oligonucleotides complementary to these windows have been made. Furthermore, using complementary oligonucleotides, in addition to the degenerate oligonucleotides and their complements, a full length double-stranded VH gene variant was assembled. The assembled gene variants have been cloned into the vector pRB500 (Example 2), which contains the pelB leader sequence for secretion. These experiments are described in Example 1.

Synthesis of these oligonucleotides and incorporation into the VH gene as described, in all possible combinations, can theoretically generate 112×2$^{25}$×4096=1.54×10$^{13}$ different peptide sequences. Due to the length of the region targeted in VH CDR2, a large number of variants are generated; however, a large proportion of the variants will have the preselected amino acids.

As an alternative to using the VH CDR2 window shown in FIG. 5a, another window encompassing a different portion of VH CDR2 was designed (FIG. 5b). In this window, certain positions in the region were selected (see Model VI below for further explanation) and subjected to walk-through mutagenesis using His as the preselected amino acid. If oligonucleotides designed as shown in FIG. 5b are used instead of the oligonucleotides of FIG. 5a, 112×128× 4096=5.87×10$^7$ different peptide sequences can be generated.

Model IV

In another embodiment using the heavy chain of the Fv molecule, a different combination of windows is used. The Asp window previously described for CDR1 (FIG. 3b; Models I, III) and the His window previously described for CDR3 (FIG. 4a; Model II) are used with a new window in which Ser is walked through the amino-terminal portion of VH CDR2 from amino acids 50–60. This walk-through mutagenesis is illustrated in FIG. 6.

Synthesis of these oligonucleotides and incorporation into the VH gene in all possible combinations can generate 112×4096×196,608=9.02×10$^{10}$ different peptide sequences.

Model V

In another embodiment, a protein with an existing catalytic activity is altered to generate a different mechanism of catalysis. In the process, the specificity and/or activity of the enzyme may also altered. The HIV protease was selected as an enzyme for mutagenesis. The HIV protease is an aspartic protease and has an Asp-Thr-Gly sequence typical of aspartic proteases which contain a conserved Asp-Thr(Ser)-Gly sequence at the active site (Toh et al., *EMBO J.* 4: 1267–1272 (1985)). For walk-through mutagenesis, the Asp-Thr-Gly sequence in the protease was selected as a target for mutagenesis. Walk-through mutagenesis was repeated three different times with three preselected amino acids, Asp, His and Ser. This approach is intended to result in the conversion of an aspartic protease into a serine protease and an alteration of the mechanism of catalysis. In addition, mutants of the HIV aspartic protease with altered activity, specificity, or an altered mechanism of catalysis are expected, altered FIG. 7 shows the three residues or window to be altered and illustrates three sequential walk-through procedures with Asp, His and Ser. At the first position, which is an Asp residue, only His and Ser are introduced. At the two remaining positions, Asp, His, and Ser are each introduced. Note that in the second position of the second codon and in the second position of the third codon, the A required in the His walk-through has already been introduced in the Asp walk-through (FIG. 7). The sequence of the mixed probe which includes 324 different sequences and the encoded amino acids are also shown in FIG. 7. This mutagenesis protocol will generate 324 different peptide sequences in the active site window.

For mutagenesis and expression of the HIV protease, plasmid pRB505 was constructed as described in Example 2. This plasmid will direct expression of the HIV protease from an inducible tac promoter (de Boer, H. A. et al., *Proc. Natl. Acad. Sci. USA* 80: 21 (1983)). In pRB505, the protease gene sequence is fused in frame to the 3' end of a sequence encoding the pelB leader sequence of pectate lyase, so that the protease can be secreted into the periplasmic space of *E. coli*. The construct is designed so that the leader sequence is cleaved and the naturally occurring N-terminal sequence of the protease is generated. Secretion of the HIV protease will facilitate assaying and purification of variants generated by mutagenesis.

The complement of the mixed probe shown in FIG. 7 was synthesized, and a partially complementary oligonucleotide was also synthesized. These oligonucleotides are designed to allow production of a double-stranded sequence with convenient XhoI (CTCGAG) and BstEII (GGTNACC) restriction sites (underlined) flanking the active site window. (Note that the complement of the active site window's coding sequence was synthesized. Thus, the nucleotide sequence for the wild type for the active site window (5'-ACC AGT GTC-3') shown below is the complement of 5'-GAC ACT GGT-3', the latter which codes for Asp-Thr-Gly.)

erates the complement of each of the variant oligonucleotides. The reaction mix was digested with BstEII and XhoI and the products were separated on an 8% polyacrylamide gel. A 106 bp band was recovered from the gel by electroelution. This band, containing the active site window fragments, was cloned between the BstEII and XhoI sites of pRB505, and the ligated plasmids were introduced into a TG1/pACYC177 lacI$^q$ strain. The resulting transformants were plated on LB amp plates, and yielded about 1000 colonies.

The colonies were screened using the protease screening assay described in Example 4. Ampicillin resistant colonies were screened for proteolytic activity by replica plating onto nutrient agar plates containing 2 mM IPTG for induction of expression, and either dry milk powder (3%) or hemoglobin as a protease substrate as described in Example 4. In this assay, if a colony secretes proteolytic activity leading to degradation of the substrate in the plate (e.g., dry milk), a zone of clearing appears against the opaque background of the plate. Because the wildtype HIV protease does not show activity in the assay (due to its substrate specificity), novel activities can be distinguished from the original activity. Preliminary data indicate that transformants with novel activity can be generated by the described procedure.

The novel variants generated can be screened further for acquisition of a different mechanism of action by differential inhibition with protease inhibitors. For example, serine proteases are inhibited by PMSF (phenylmethylsulfonyl fluoride), DFP (diisopropylphosphofluoridate), TLCK (L-1-chloro3-(-9-tosylamide)-7-amino-2-heptanonehydrochloride). Transformants which generate a halo on plates can be grown in liquid media, and extracts from the cultures can be assayed in the presence of the appropriate inhibitors. Reduced activity in the presence of a serine protease inhibitor as compared to activity in the absence of such an inhibitor will be indicative that a variant functions with a serine protease catalytic mechanism. Among the variants generated by the walk-through mutagenesis procedure will be variants with altered activity, altered specificity, a serine protease mechanism or a combination of these features. These variants can be further characterized using known techniques.

Model VI

In this embodiment, walk-through mutagenesis of five out of six CDRs of the MCPC 603 Fv molecule is performed, and Asp, His and Ser are the preselected amino acids. In this model, "walk-through" mutagenesis is carried out from two to three times with a different amino acid in a given region or domain. For example, Ser and His are sequentially walked-through VL CDR1 (FIG. 8a), and Asp and Ser are sequentially walked-through VL CDR3 (FIG. 8b). VL CDR2 was not targeted for mutagenesis because structural

```
                     G    TC   G
                     TT   CG   GA
5'-  CAT TTC  CTC GAG AAC GGT GTC ATC AGC ACC AGT GTC —
                     --- WINDOW ---

CAG CAG AGC TTC CTT TAG TTG ACC ACC GAT TTT GAT GGT —
                     3'-TA      AAA CTA CCA

AAC CAG TGG - 3'
TTG GTC ACC TGC GAC GGT GTC TCA CTA AAC G-5'
```

The oligonucleotides were annealed and extended in a reaction using the Klenow fragment of DNA polymerase. Extension of the short complementary oligonucleotide genstudies indicated that this region contributes little to the binding site in MCPC 603.

In CDR1 of the VH chain of the Fv, Asp and His are walked through (FIG. 8c). Ser can be introduced at two positions in CDR1 with a single base change (FIG. 8c, positions 32 and 33). In VH CDR2, His and Ser are the preselected amino acids used (FIG. 8d) and in VH CDR3, Asp, His and Ser are each walked through the amino terminal five positions of CDR3 (FIG. 8e).

Furthermore, in this embodiment not all amino acids in a given region are mutagenized, although they do not contain the preselected amino acid as the wild type residue. For example, in FIG. 8d, only positions 50, 52, 56, 58 and 60 are mutagenized. Similarly, in FIGS. 8a–d, it can be seen that one or more residues in the region are not mutagenized. Mutagenesis of noncontiguous residues within a region can be desirable if it is known, or if one can guess, that certain residues in the region will not participate in the desired function. In addition, the number of variants can be minimized.

For example, in the case of a serine protease, a design factor is the distance between the the preselected amino acids. In order to form a catalytic triad, the residues must be able to hydrogen bond with one another. This consideration can impose a proximity constraint on the variants generated. Thus, only certain positions within the CDRs may permit the amino acids of the catalytic triad to interact properly. Thus, molecular modeling or other structural information can be used to enrich for functional variants.

In this case, known structural information was used to identify residues in the regions that may be close enough to permit hydrogen bonding between Asp, His and Ser, as well as the range of residues to be mutagenized. Roberts et al. have identified regions of close contact between portions of the CDRs (Roberts, V. A. et al., *Proc. Natl. Acad. Sci. USA* 87: 6654–6658 (1990)). This information together with data from the x-ray structure of MCPC 603 were used to select promising areas of close contact among the CDRs targeted for mutagenesis.

If the mutagensis is carried out as illustrated and the regions are randomly combined, then 17,280×27,648×432× 2304×7776=5.2×10$^{18}$ different peptide sequences can be generated.

Model VII

In each of the embodiments described above, mutagenesis is designed to create clusters of catalytically active residues. In the embodiment of Model VII, mutagenesis is designed to create a novel binding function. In this embodiment, residues implicated in the binding or chelating of a co-factor (e.g., Fe +++) are introduced into regions of a molecule, in this case MCPC 603. Many enzymes use metal ions as cofactors, so it is desirable to generate such binding sites as a first step towards engineering such enzymes.

In this embodiment two histidine and two tyrosine residues are introduced into the CDRs of MCPC 603. Dioxygenases, which are members of the class of oxidoreductases, and which catalyze the oxidative cleavage of double bonds in catachols contain a bound iron at their active sites. Spectroscopic analysis and X-ray crystallography indicate that the ferric ion at the active site of the dioxygenases is bound by two tyrosine and two histidine residues.

The histidine windows designed for MCPC 603 (see e.g., FIG. 3c, VL CDR2; FIG. 4a, VH CDR3; and FIG. 5a, VH CDR2) can be used to introduce histidine residues into one or more domains of MCPC 603 or additional windows can be designed. Similarly, the one or more CDRs of MCPC 603 can be targeted for walk-through mutagenesis with tyrosine. Using these cassettes, variants with 2 histidine and 2 tyrosine residues in a large variety of combinations and in different regions can be produced.

These variants can be screened for acquisition of metal binding. For example, pools of colonies can be grown and a periplasmic fraction can be prepared. The proteins in a the periplasmic fraction of a given pool can be labeled with an appropriate radioactive metal ion (e.g., $^{55}$Fe) and the presence of a metal binding variant can be determined using high sensitivity gel filtration. The presence of radioactivity in the protein fraction from gel filtration is indicative of metal binding. Pools can be subdivided and the process repeated until a mutant is isolated.

Alternatively, a nitrocellulose filter assay can be used. Colonies of a strain which secretes the mutant proteins and which allows the proteins to leak into the medium can be grown on nitrocellulose filters. The mutant proteins leaking from the colonies can bind to the nitrocellulose and the presence of metal binding proteins can be ascertained by probing with radiolabeled metal ions.

Generation of a metal binding in the VL chain could provide a metal binding site for a catalytic VH chain. Production of Fv from these component chains could allow enhancement of catalysis mediated by one chain by co-factor binding in the other chain.

The present invention is further illustrated in the following examples.

EXAMPLE 1

Construction of a VH Variant

Oligonucleotide Synthesis

β-cyanoethyl phosphoramidites and polymer support (CPG) columns were purchased form Applied Biosystems, Inc. (Foster City, Calif.). Anhydrous acetonitrile was purchased form Burdick and Jackson (Part no. 015-4). Oligonucleotides were synthesized on an Applied Biosystems Model 392 using programs provided by the manufacturer (Sinha, N. D., et al., *Nucleic Acids Res.*, 12: 4539 (1984)). On completion of the synthesis, the oligonucleotide was freed from the support and the protecting cyanoethyl groups were removed by incubation in concentrated NH$_4$OH. Following electrophoresis on a 10% polyacrylamide gel, oligomers were excised from the gel, electroeluted, purified on C18 columns, freeze dried and dissolved in the appropriate buffer at a final concentration of 1 µg/ml.

Oligonucleotides

In order to construct the VH variant described in Model III, the following oligonucleotides and their complements (also shown), ranging in length from 30–54 bases were designed and synthesized as described. Codon utilization was adjusted to reflect the most frequently used *E. coli* codons.

A/a: 910372/910373

5'- AAG AAT TCC ATG GAA GTT AAA CTG GTA GAG -3'

5'- ACC ACC AGA CTC TAC CAG TTT AAC TTC CAT GGA ATT—
CTT- 3'

B/b: 910374/910375

5'- TCT GGT GGT GGT CTG GTA CAG CCG GGT GGA TCC—
CTG- 3'

5'- AGA CAG ACG CAG GGA TCC ACC CGG CTG TAC CAG—
ACC -3'

C/c: 910376/910377

5'- CGT CTG TCT TGC GCT ACC TCA GGT TTC -3'

5'- AGA GAA GGT GAA ACC TGA GGT AGC GCA -3'

D/d: 910378/910379

```
                GA  G   GAT   T
5'-ACC TTC TCT GAC TTC TAC ATG GAG TGG GTA CGT—
CAG-3'

A   ATC   C   TC
5'-ACC CGG GGG CTG ACG TAC CCA CTC CAT GTA GAA—
GTC -3'
```

E/e: 910380/910381

5'-CCC CCG GGT AAA CGT CTC GAG TGG ATC GCA GCT—
AGC- 3'

5'-GTT ACG GCT AGC TGC GAT CCA CTC GAG ACG TTT -3'

F/f: 910382/910383

```
            CA  C    C T C   CA  C T C   CA
5'-CGT AAC AAA GGT AAC AAG TAT ACT GAA TAC AGC—

CA  CA  CA  C  C CA
GCT TCT GTT AAA GGT GGT-3'

TG G  G  TG TG   TG TG   G A G  TG
5'-GAT GAA ACG ACC TTT AAC AGA AGC GCT GTA TTC AGT—

TG   G A G   G  TG
AGT ATA CTT GTT ACC TTT -3'
```

G/g: 910384/910385

5'-TTC ATC GTT TCT CGT GAC ACT AGT CAA TCG ATC CTG—
TAC CTG- 3'

5'- ATT CAT CTG CAG GTA CAG GAT CGA TTG ACT AGT GTC—
ACG AGA AAC- 3'

H/h: 910386/910387

5'-CAG ATG AAT GCA TTG CGT GCT GAA GAC ACC GCT ATC—
TAC- 3'

5'-CGC GCA GTA GTA CAT AGC GGT GTC TTC AGC ACG CAA—
TGC- 3'

I/i: 910388/910389 OR 9104103/9104104

```
                    G   C   C   A           G   C   C
5'-TAC TGC GCG CGT AAC TAC TAT GGC AGC ACT TGG TAC—

C   TC  TC
TTC GAC GTT TGG -3'

GA  GA  G   G   G   C           T
5'-ACC TGC ACC CCA AAC GTC GAA GTA CCA AGT GCT GCC

G   G   C
ATA GTA CTT-3'
```

J/j: 910390/910391

```
5'-GGT GCA GGT ACC AAC GTT ACC GTT TCT TGA TAG CAG—
GTA AGC TTA A -3'

5'-TTA AGC TTA CCT GCT ATC AAG AAA CGG TAA CGG TGG
T -3'
```

Gene Assembly

These pairs of oligonucleotides can be assembled into a VH gene as depicted below:

```
A    B    C    D    E    F    G    H    I    J a    b    c    d    e    f    g    h    i    j
```

Pairs D/d, F/f, and I/i are degenerate and complementary oligonucleotides encompassing the "windows" depicted in FIG. 3a, FIG. 5a, and FIG. 3b, respectively. The design of the other oligonucleotides was similar to that described by Pluckthun et al., and included the introduction of a series of restriction sites (EcoRI, NcoI, BamHI, SauI, XmaI, XhoI, NheI, AccI, HaeII, SpeI, ClaI, PstI, NsiI, BssHII, KpnI, and HindIII useful for further manipulations (see Pluckthun, A. et al., Cold Spring Harbor Symp. Biol., Vol. LII, 105–112 (1987)). For gene assembly (Alvarado-Urbina, G. et al., Biochem. Cell. Biol. 64: 548–555 (1986)), eighteen of the oligonucleotides (B-I, b-i) were phosphorylated using T4 polynucleotide kinase. Each of ten complementary pairs was annealed separately. The annealed pairs were then mixed and ligated together using T4 DNA ligase. The product is shown schematically below:

```
EcoRI NcoI                              HindIII
_____

----      ----      ----
     CDR1      CDR2      CDR3
```

The synthetic gene was designed to contain restriction sites for cloning. Following ligation, the fully assembled molecules were cleaved with NcoI and HindIII, gel purified, and inserted into vector pRB500 (see Example 2) at the NcoI and HindIII sites. About 1500 tranformants above the background were obtained on LB amp plates. The resulting constructs should contain the VH gene variants fused in frame to the pelB signal peptide.

EXAMPLE 2

Construction of pRB505

Construction of RB500

Two complementary oligonucleotides which code for the pelB leader sequence (Lei, S. P. et al., J. Bacteriol. 169: 4379 (1987)) were chemically synthesized. The oligonucleotides, which were designed to have 5' and 3' overhangs complementary to NcoI and PstI sites, were hybridized and cloned into the PstI and NcoI sites of vector pKK233.2 (Pharmacia). The oligonucleotides are shown below:

```
5'- C ATG AAA TAC CTA TTG CCT ACG GCA GCC GCT GCA—
   3'-   TTT ATG GAT AAC GGA TGC CGT CGG CGA CGT

TTG TTA TTA GCT GCC CAA CCA GCC ATG GCG AAT TCC—
AAC AAT AAT CGA CGG GTT GGT CGG TAC CGC TTA AGG

CTG CA-3'

G  -5'
```

The resulting plasmid. pRB500 has an inducible tac promoter upstream of the ATG start codon of the pelB sequence. There is a unique NcoI site (underlined) at the 31' end of the sequence coding for the pelB leader into which a gene encoding a product to be secreted, such as the HIV protease or the $V_H$ or $V_L$ regions of an antibody, may be inserted. (The NcoI site ligated to the 5' overhang of the fragment is not regenerated.)

Construction of pB503

The HIV protease gene was obtained from pUC18.HIV (Beckman, catalog #267438). The gene can be excised from this plasmid as a HindIII-EcoRI or HindIII-BamHI fragment. However, the HindIII site in the HIV protease cannot be directly cloned in frame to the pelB leader sequence present in plasmid pRB500. Therefore, a double-stranded oligonucleotide linker was designed so that the amino terminal methionine of the HIV protease coding sequence could be joined in frame to the coding sequence of the pelB leader peptide in pRB505. The following sequence was synthesized:

```
                    Met Ala Pro Gln Ile Thr . . .
5'- AG CTT GCC ATG GCG CCG CAA ATC ACT CT-3'
3'-  A CGG TAC CGC GGC GTT TAG TG -5'
            NcoI
```

This linker has a 5'- HindIII overhang and 3' DraIII overhang. The oligonucleotide was cloned into the unique HindIII and DraIII sites in pUC18.HIV. The resulting plasmid is called pRB503. The linker introduces an NcoI site into the vector at the initiator methionine of the HIV protease and reconstructs the sequence as found in pUC18.HIV.

Construction of pRB505

The HIV protease gene was isolated from pRB503 as an NcoI-EcoRI fragment and was cloned into the unique NcoI and EcoRI sites of pRB500. In the final construct, the HIV protease is fused in frame to the pelB leader sequence, and expression is driven by the inducible tac promoter. It is expected that the leader peptidase will cleave the fusion protein between Ala and Pro (residues 2 and 3 above) of the HIV sequence, thereby generating an N-terminal proline just as in the wild type HIV protease.

EXAMPLE 3
Walk-Through Mutagenesis of the HIV Protease Active Site

A degenerate oligonucleotide which spans the Asp-Thr-Gly active site residues of the HIV protease was designed and synthesized. This oligonucleotide has a sequence complementary to that shown in FIG. 7.

```
                        G   TC  G
                        TT  CG  GA
5'-  CAT TTC CTC GAG AAC GGT GTC ATC AGC ACC AGC GTC—
CAG CAG AGC TTC CTT TAG TTG ACC ACC GAT TTT GAT GGT—
AAC CAG TGG -3'
```

A second oligonucleotide, partially complementary to the above sequence was synthesized to permit conversion of the above degenerate oligonucleotides to double-stranded form. The complementary oligonucleotide had the following sequence:

```
5'-  GCA AAT CAC TCT GTG GCA GCG TCC ACT GGT TAC CAT—
CAA AAT -3'
```

The degenerate oligonucleotides and complementary oligonucleotides were annealed.

```
                            G   TC  G
                            TT  CG  GA
5'-  CAT TTT CTC GAG AAC GGT GTC ATC AGC ACC AGT GTC—
              XhoI
     CAG CAG AGC TTC CTT TAG TTG ACC ACC GAT TTT GAT—
                                        3'- TA AAA CTA—
     GGT AAC CAG TGG -3'
     CCA TTG GTC ACC TGC GAC GGT GTC TCA CTA AAC G -5'
```

The oligos were extended using the Klenow fragment of DNA polymerase. (Oliphant, A. R. and Struhl, K., *Methods Enzymol.*, 155: 568–582 (1987)). The resulting mixture was cleaved with BstEII and XhoI, and separated on an 8% polyacrylamide gel. A 106 bp band containing the active site windows was isolated by electroelution from a gel slice, extracted with phenol:chloroform, and ethanol precipitated.

Vector pRB505 was cleaved with BstEII and XhoI and then treated with calf intestinal alkaline phosphatase to prevent religation. The vector band was purified from a low-melting agarose gel. The purified BstEII-XhoI active site windows (100 nanograms) were cloned into the BstEII and XhoI sites of pRB505 (500 nanograms). The ligation mix was used to transform a TG1/pACYC177 lacI$^q$ strain and amplicillin resistant transformants were selected on LB amp plates (LB plus 50 µg/ml ampicillin; Miller, J. H., (1972), In: *Experiments in Molecular Genetics, Cold Spring Harbor Laboratory* (Cold Spring Harbor, N.Y.), p. 433. Approximately 1000 transformants were obtained by this procedure. Several of these transformants were tested for novel activity using the protease plate assay described below in Example 4.

EXAMPLE 4

Protease Activity Plate Assays

Sensitivity of the Plate Assay

In the case where the activity to be assayed is a proteolytic activity, substrate-containing nutrient plates can be used for screening for colonies which secrete a protease. Protease substrates such as denatured hemoglobin can be incorporated into nutrient plates (Schumacher, G. F. B. and Schill, W. B., *Anal. Biochem.*, 48: 9–26 (1972); Benyon and Bond, *Proteolytic Enzymes*, 1989 (IRL Press, Oxford) p. 50). When bacterial colonies capable of secreting a protease are grown on these plates, the colonies are surrounded by a clear zone, indicative of digestion of the protein substrate present in the medium.

A protease must meet several criteria to be detected by this assay. First, the protease must be secreted into the medium where it can interact with the substrate. Second, the protease must cleave several peptide bonds in the substrate so that the resulting products are soluble, and a zone of clearing results. Third, the cells must secrete enough protease activity to be detectable above the threshold of the assay. As the specific activity of the protease decreases, the threshold amount required for detection in the assay will increase.

One or more protease substrates may be used. For example, hemoglobin (0.05–0.1%), casein (0.2%), or dry milk powder (3%) can be incorporated into appropriate nutrient plates. Colonies can be transferred from a master plate using and inoculating manifold, by replica-plating or other suitable method, onto one or more assay plates containing a protease substrate. Following growth at 37° C. (or the appropriate temperature), zones of clearing are observed around the colonies secreting a protease capable of digesting the substrate.

Four proteases of different specificities and reaction mechanisms were tested to determine the range of activities detectable in the plate assay. The enzymes included elastase, subtilisin, trypsin, and chymotrypsin. Specific activities (elastase, 81U/mg powder; subtilisin, 7.8 U/mg powder; trypsin, 8600 U/mg powder; chymotrypsin, 53 U/mg powder) were determined by the manufacturer. A dilution of each enzyme, elastase, subtilisin, trypsin, and chymotrypsin, was prepared and 5 µl aliquots were pipetted into separate wells on each of three different assay plates.

Plates containing casein, dry milk powder, or hemoglobin in a 1% Difco bacto agar matrix (10 ml per plate) in 50 mM Tris, pH 7.5, 10 mM CaCl$_2$ buffer were prepared. On casein plates (0.2%), at the lowest quantity tested (0.75 ng of protein), all four enzymes gave detectable clearing zones under the conditions used. On plates containing powdered milk (3%), elastase and trypsin were detectable down to 3 ng of protein, chymotrypsin was detectable to 1.5 ng, and subtilisin was detectable at a level of 25 ng of protein spotted. On hemoglobin plates, at concentrations of hemoglobin ranging from 0.05 and 0.1 percent, 1.5 ng of elastase, trypsin and chymotrypsin gave detectable clearing zones. On hemoglobin plates, under the conditions used, subtilisin did not yield a visible clearing zone below 6 ng of protein.

Assay of Variant of HIV Protease

Of the approximately 1000 ampicillin resistant transformants obtained by the procedure described in Example 3, 300 colonies were screened using the protease plate screening assay. The ampicillin resistant colonies were screened for proteolytic activity by replica plating onto nutrient agar plates (LB plus ampicillin) with a top layer containing IPTG (isopropylthiogalactopyranoside) for induction of expression, and either dry milk powder (3%) or hemoglobin as a protease substrate.

Protease substrate stock solutions were made by suspending 60 mg of hemoglobin or 1.8 g of powdered milk in 10 ml of deionized water and incubating at 60° C. for 20 minutes. The top layer was made by adding ampicillin and IPTG to 50 ml of melted LB agar (15 g/l) at 60° C. to final concentrations of 50 µg/ml and 2 mM, respectively, and 10 ml of protease substrate stock solution. 10 ml of the top layer was layered onto LB amp plates.

Colonies secreting sufficient proteolytic activity which degrades the particular substrate in the plate (e.g., dry milk) will have a zone of clearing around them which is distinguishable from the opaque background of the plate. Whereas none of the transformants gave a zone of clearing on hemoglobin plates, a large proportion of the transformants gave a zone of clearance on dry milk powder plates. Note that the dry milk powder plates had been incubated at 37° C. for about 1.5 days and then refrigerated. Although no halos appeared after the 1.5 day incubation at 37° C., more than 90% of the colonies on the assay plates had halos after 3 days in the refrigerator. Three sample colonies which produced halos on the assay plate were streaked onto dry milk powder plates containing 2 mM IPTG. Two of the three streaks grew. Distinct zones of clearing were again observed for these two isolates under the same conditions (grown overnight at 37° C., followed by refrigeration for three days). As a control, transformants of TG1/pACYC177 lacI$^q$ containing either pRB500, which encodes the pelB signal sequence, but no HIV protease, or containing pRB505, which encodes the pelB signal sequence fused to the "wild type" HIV protease, were also streaked onto dry milk powder plates with 2 mM IPTG. In contrast to the transformants obtained from the mutagenesis, these control transformants did not give a zone of clearance on dry milk powder plates. This observation is consistent with previous results indicating that retroviral proteases are selective for viral target proteins (Skalka, A. M., *Cell* 56: 911–913 (1984)). Using this assay novel protease activities generated by the walk-through mutagenesis procedure can be differentiated from the wild type HIV protease by altered substrate specificities.

Equivalents

Those skilled in the art will recognize, or be able to ascertain using no more than routine experimentation, many equivalents to the specific embodiments of the invention described herein. Such equivalents are intended to be encompassed by the following claims.

I claim:

1. A method of mutagenesis of a gene encoding a protein, comprising:
   a) selecting one or more defined region(s) of the amino acid sequence of the protein encoded by the gene to be mutagenized;
   b) for each of the defined region(s), determining one or more amino acid residue(s) to be inserted into amino acid positions in the defined region;
   c) synthesizing without saturation a mixture of oligonucleotides, comprising a nucleotide sequence for each defined region, wherein each oligonucleotide contains, at each sequence position in the defined region, either a nucleotide required for synthesis of the protein to be mutagenized or a nucleotide required for a codon of one of the predetermined amino acid(s), the mixture containing all possible variant oligonucleotides according to this criterion; and
   d) generating an expression library of cloned genes containing said oligonucleotides.

2. A method of claim 1, wherein the defined region comprises a functional domain of the protein.

3. A method of claim 1, wherein the defined region comprises a domain at or around the catalytic site of an antibody.

4. A method of claim 1, wherein the defined region comprises a hypervariable region of an antibody.

5. A method of claim 1, wherein the predetermined amino acid is Ser, Thr, Asn, Gln, Tyr, Cys, His, Glu, Asp, Lys or Arg.

6. The method of claim 1, wherein about 12.5% to 100% of the oligonucleotides prepared in step (c) contain at least one codon for a predetermined amino acid.

7. The method of claim 1, wherein at least about 25% of the oligonucleotides prepared in step (c) contain at least one codon for a predetermined amino acid.

8. The method of claim 1, wherein at least about 50% of the oligonucleotides prepared in step (c) contain at least one codon for a predetermined amino acid.

9. The method of claim 1 wherein for at least one defined region, three amino acid residues to be inserted into amino acid positions in said region are determined.

10. The method of claim 1 wherein for at least one defined region, two amino acid residues to be inserted into amino acid positions in said region are determined.

11. The method of claim 1 wherein for at least one defined region, a single amino acid residue to be inserted into amino acid positions in said region is determined.

12. A library of cloned genes prepared by the method of claim 1.

13. A method of mutagenesis of a gene encoding a protein, comprising:
   a) selecting a defined region of the amino acid sequence of the protein encoded by the gene to be mutagenized;
   b) determining two amino acid residues to be inserted into amino acid positions in said defined region;
   c) synthesizing without saturation a mixture of oligonucleotides, comprising a nucleotide sequence for the defined region, wherein about 12.5% to 100% of the oligonucleotides prepared contain at least one codon for either of the two predetermined amino acids, and wherein each oligonucleotide contains, at each sequence position in the defined region, either a nucleotide required for synthesis of the protein to be mutagenized or a nucleotide required for a codon of one of the two predetermined amino acids, the mixture containing all possible variant oligonucleotides according to this criterion; and
   d) generating an expression library of cloned genes containing said oligonucleotides.

14. A method of claim 13, wherein the defined region comprises a functional domain of the protein.

15. A method of claim 13, wherein the defined region comprises a domain at or around the catalytic site of an antibody.

16. A method of claim 13, wherein the defined region comprises a hypervariable region of an antibody.

17. A method of claim 13, wherein the predetermined amino acid is Ser, Thr, Asn, Gln, Tyr, Cys, His, Glu, Asp, Lys or Arg.

18. The method of claim 13, wherein at least about 25% of the oligonucleotides prepared in step (c) contain at least one codon for either of the two predetermined amino acids.

19. The method of claim 13, wherein at least about 50% of the oligonucleotides prepared in step (c) contain at least one codon for either of the two predetermined amino acids.

20. A library of cloned genes prepared by the method of claim 13.

21. A method of mutagenesis of a gene encoding a protein, comprising:
   a) selecting a defined region of the amino acid sequence of the protein encoded by the gene to be mutagenized;
   b) determining a single amino acid residue to be inserted into amino acid positions in the defined region;
   c) synthesizing without saturation a mixture of oligonucleotides, comprising a nucleotide sequence for the defined region, wherein about 12.5% to 100% of the oligonucleotides prepared contain at least one codon for the predetermined amino acid, and wherein each oligonucleotide contains, at each sequence position in the defined region, either a nucleotide required for synthesis of the protein to be mutagenized or a nucleotide required for a codon of the predetermined amino acid, the mixture containing all possible variant oligonucleotides according to this criterion; and
   d) generating an expression library of cloned genes containing said oligonucleotides.

22. A method of claim 21, wherein the defined region comprises a functional domain of the protein.

23. A method of claim 21, wherein the defined region comprises a domain at or around the catalytic site of an antibody.

24. A method of claim 21, wherein the defined region comprises a hypervariable region of an antibody.

25. A method of claim 21, wherein the predetermined amino acid is Ser, Thr, Asn, Gln, Tyr, Cys, His, Glu, Asp, Lys or Arg.

26. The method of claim 21, wherein at least about 50% of the oligonucleotides prepared in step (c) contain at least one codon for a predetermined amino acid.

27. A library of cloned genes prepared by the method of claim 21.

28. A method of producing a mixture of oligonucleotides for mutagenesis without saturation of a nucleotide sequence encoding a selected region of a protein to introduce a predetermined amino acid at each position in the region, comprising synthesizing a mixture of oligonucleotides comprising the nucleotide sequence for the preselected region, wherein each oligonucleotide contains, at each sequence position in the selected region, either a nucleotide required for synthesis of the amino acid of the region or a nucleotide required for a codon of the predetermined amino acid, the resulting mixture containing all possible variant oligonucleotides containing either of the two nucleotides at each position.

29. A mixture of oligonucleotides produced by the method of claim 28, wherein about 12.5% to 100% of the oligonucleotides contain at least one codon for a single, predetermined amino acid.

30. A method of identifying a gene encoding a protein having a desired structure or function, comprising:
- a) selecting one or more defined region(s) of the amino acid sequence of the protein encoded by a gene to be mutagenized;
- b) for each of the defined region(s), determining one or more amino acid residue(s) to be inserted into amino acid positions in the defined region;
- c) synthesizing without saturation a mixture of oligonucleotides, comprising a nucleotide sequence for the defined region, wherein each oligonucleotide contains, at each sequence position in the defined region, either a nucleotide required for synthesis of the protein to be mutagenized or a nucleotide required for a codon of one of the predetermined amino acid(s), the mixture containing all possible variant oligonucleotides according to this criterion;
- d) generating an expression library of cloned genes containing said oligonucleotides; and
- e) screening the library to detect a clone encoding a mutant protein having the desired structure or function.

31. The method of claim 30, wherein for at least one defined region, three amino acid residues to be inserted into amino acid positions in the region are determined.

32. The method of claim 30, wherein for at least one defined region, two amino acid residues to be inserted into amino acid positions in the region are determined.

33. The method of claim 30, wherein for at least one defined region, a single amino acid residue to be inserted into amino acid positions in the region is determined.

* * * * *

UNITED STATES PATENT AND TRADEMARK OFFICE
CERTIFICATE OF CORRECTION

PATENT NO. : 5,798,208
DATED : August 25, 1998
INVENTOR(S) : Roberto Crea

It is certified that error appears in the above-identified patent and that said Letters Patent is hereby corrected as shown below:

In Column 29, line 31:  After the word "catalytic", delete "site of an antibody" and insert therefor --site of an enzyme or a binding domain--;

In Column 30, line 14:  After the word "catalytic", delete "site of an antibody" and insert therefor --site of an enzyme or a binding domain--; and In Column 30, line 52:  After the word "catalytic", delete delete "site of an antibody" and insert therefor --site of an enzyme or a binding domain--.

Signed and Sealed this

Twenty-second Day of December, 1998

Attest:

BRUCE LEHMAN

Attesting Officer　　　　　Commissioner of Patents and Trademarks